United States Patent
Sakai et al.

(10) Patent No.: US 11,160,473 B2
(45) Date of Patent: Nov. 2, 2021

(54) BIOLOGICAL INFORMATION MEASUREMENT DEVICE AND NON-TRANSITORY COMPUTER READABLE MEDIUM

(71) Applicant: FUJIFILM BUSINESS INNOVATION CORP., Tokyo (JP)

(72) Inventors: Kazuhiro Sakai, Tokyo (JP); Manabu Akamatsu, Tokyo (JP); Tomoaki Kojima, Tokyo (JP); Hideaki Ozawa, Tokyo (JP); Hideyuki Umekawa, Tokyo (JP)

(73) Assignee: FUJIFILM BUSINESS INNOVATION CORP., Tokyo (JP)

( * ) Notice: Subject to any disclaimer, the term of this patent is extended or adjusted under 35 U.S.C. 154(b) by 166 days.

(21) Appl. No.: 16/285,247

(22) Filed: Feb. 26, 2019

(65) Prior Publication Data
US 2019/0290174 A1 Sep. 26, 2019

(30) Foreign Application Priority Data
Mar. 23, 2018 (JP) .............................. JP2018-057113

(51) Int. Cl.
*A61B 5/1455* (2006.01)
*A61B 5/00* (2006.01)
*A61B 5/026* (2006.01)

(52) U.S. Cl.
CPC ........ *A61B 5/14551* (2013.01); *A61B 5/0059* (2013.01); *A61B 5/7214* (2013.01); *A61B 5/0261* (2013.01)

(58) Field of Classification Search
CPC ............ A61B 5/14551; A61B 5/14542; A61B 5/1455; A61B 5/02; A61B 5/0059;
(Continued)

(56) References Cited

U.S. PATENT DOCUMENTS 5,246,002 A * 9/1993 Prosser .............. A61B 5/14551
356/41
7,184,809 B1 * 2/2007 Sterling ............. A61B 5/14551
600/322

(Continued)

FOREIGN PATENT DOCUMENTS

JP  2006-231012  9/2006
WO  WO-2016193735 A1 * 12/2016 ........... A61B 5/0077

OTHER PUBLICATIONS

Wijshoff. "On photoplethysmography artifact reduction and applications", Sep. 6, 2016, Technische Universiteit Eindhoven. (Year: 2016).*

*Primary Examiner* — Chu Chuan Liu
(74) *Attorney, Agent, or Firm* — Volpe Koenig

(57) ABSTRACT

A biological information measurement device includes a correction unit that receives a first signal expressing a change in an amount of light of a first wavelength detected from a living body and a second signal expressing a change in an amount of light of a second wavelength detected from the living body, and corrects at least one of the first signal and the second signal to reduce a difference between an amount of change in the first signal and an amount of change in the second signal associated with a change in an amount of arterial blood of the living body, and a computing unit that computes a change in a blood oxygen concentration in the living body on a basis of the first signal and the second signal of which at least one is corrected by the correction unit.

14 Claims, 24 Drawing Sheets

(58) Field of Classification Search
CPC . A61B 5/0261; A61B 5/0205; A61B 5/14552; A61B 5/72; A61B 5/7203; A61B 5/7207; A61B 5/7214; A61B 5/7221
USPC ........................................................ 600/323
See application file for complete search history.

(56) References Cited

U.S. PATENT DOCUMENTS

| | | |
|---|---|---|
| 7,376,452 B2 | 5/2008 | Kobayashi et al. |
| 2007/0260132 A1* | 11/2007 | Sterling ................... A61B 5/00 600/336 |
| 2013/0066174 A1* | 3/2013 | Addison ............ A61B 5/14551 600/324 |
| 2017/0273631 A1* | 9/2017 | Sakai ...................... A61B 5/725 |
| 2018/0000359 A1* | 1/2018 | Watanabe ........... A61B 5/14552 |

\* cited by examiner

BIOLOGICAL INFORMATION MEASUREMENT DEVICE AND NON-TRANSITORY COMPUTER READABLE MEDIUM

CROSS-REFERENCE TO RELATED APPLICATIONS

This application is based on and claims priority under 35 USC 119 from Japanese Patent Application No. 2018-057113 filed Mar. 23, 2018.

BACKGROUND

(i) Technical Field

The present disclosure relates to a biological information measurement device and a non-transitory computer readable medium.

(ii) Related Art

Japanese Unexamined Patent Application Publication No. 2006-231012 describes an oxygen transport circulation time measurement method that computes a change in oxygen saturation on the basis of an arterial blood absorbance signal computed from a living body using a sensor. The oxygen transport circulation time measurement method changes the amount of oxygen inhaled by the living body while also treating the point in time at which the amount changes as a reference point, and measures the amount of time from the reference point until the oxygen saturation in arterial blood changes.

SUMMARY

Meanwhile, cardiac output is one indicator that indicates the state of cardiac function. A typical method of measuring cardiac output is the thermodilution method that performs a measurement by injecting cold water from a catheter inserted into a blood vessel, but the thermodilution method is highly invasive into the living body, and the burden on the living body is large.

In contrast, with the oxygen transport circulation time measurement method, multiple light emitters that radiate light of different wavelengths are made to emit light at a living body, and the change in the blood oxygen concentration is measured from the change in the amount of light transmitted or reflected by the living body. This method is desirable for being relatively non-invasive with respect to the living body and for imposing little burden on the living body, but changes in the amplitude ratio (light dimming ratio) of the signal expressing each change in the amount of light from multiple lights detected from the living body are detected as changes in the blood oxygen concentration. In this case, for example, for a living body having an atrial fibrillation, a living body with reduced blood flow due to the influence of factors such as environmental temperature and mental state, and the like, accurately measuring the blood oxygen concentration may be difficult in some situations.

Aspects of non-limiting embodiments of the present disclosure relate to a biological information measurement device and a biological information measurement program capable of measuring changes in the blood oxygen concentration accurately compared to the case of detecting changes in the amplitude ratio (light dimming ratio) of a signal expressing each change in the amount of light from multiple lights detected from a living body as changes in the blood oxygen concentration.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided a biological information measurement device including: a correction unit that receives a first signal expressing a change in an amount of light of a first wavelength detected from a living body and a second signal expressing a change in an amount of light of a second wavelength detected from the living body, and corrects at least one of the first signal and the second signal to reduce a difference between an amount of change in the first signal and an amount of change in the second signal associated with a change in an amount of arterial blood of the living body, and a computing unit that computes a change in a blood oxygen concentration in the living body on a basis of the first signal and the second signal of which at least one is corrected by the correction unit.

BRIEF DESCRIPTION OF THE DRAWINGS

An exemplary embodiment of the present disclosure will be described in detail based on the following figures, wherein.

DETAILED DESCRIPTION

Hereinafter, one example of an exemplary embodiment for carrying out the present disclosure will be described in detail and with reference to the drawings.

First Exemplary Embodiment

Figure 1:
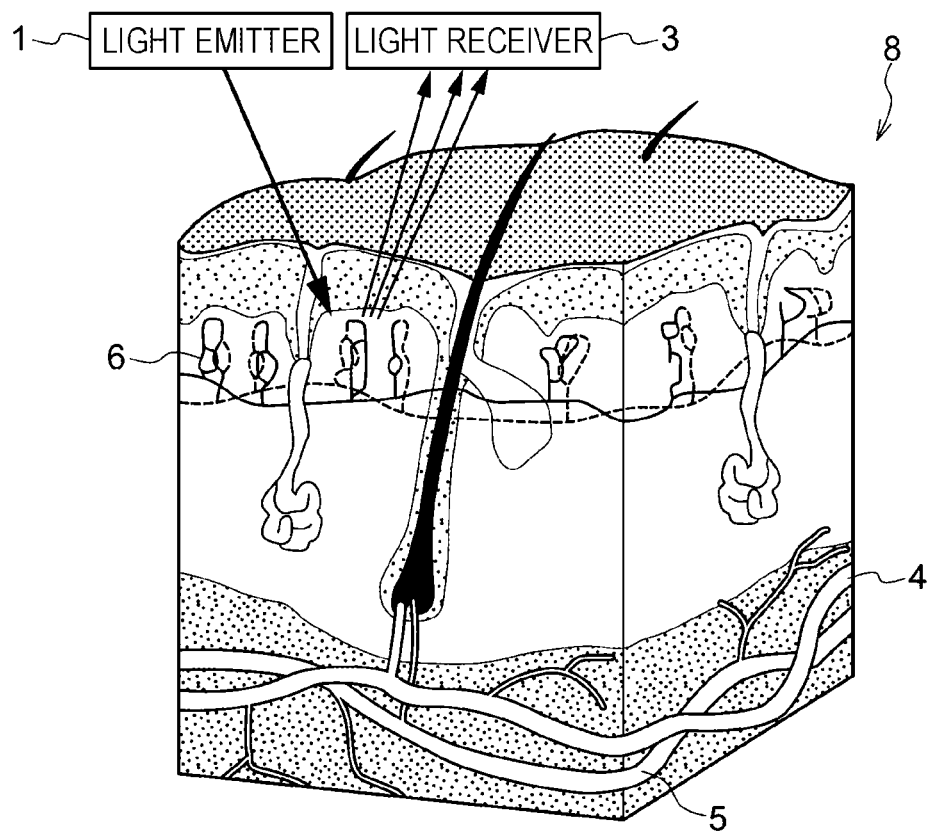
FIG. 1 is a schematic diagram illustrating an example of measuring blood flow information and oxygen saturation in the blood according to the present exemplary embodiment.

First, FIG. 1 will be referenced to describe a method of measuring blood flow information and oxygen saturation in the blood, which are one example of biological information, particularly biological information related to blood.

FIG. 1 is a schematic diagram illustrating an example of measuring blood flow information and oxygen saturation in the blood according to the present exemplary embodiment.

As illustrated in FIG. 1, the blood flow information and the oxygen saturation in the blood are obtained by irradiating a body of a patient (living body 8) with light from a light emitter 1, and measuring the intensity of light reflected from or transmitted through arteries 4, veins 5, capillaries 6, and the like running through the inside of the living body 8 received by a light receiver 3, or in other words, the amount of reflected light or transmitted light received.

(Measurement of Blood Flow Information)

Figure 2:
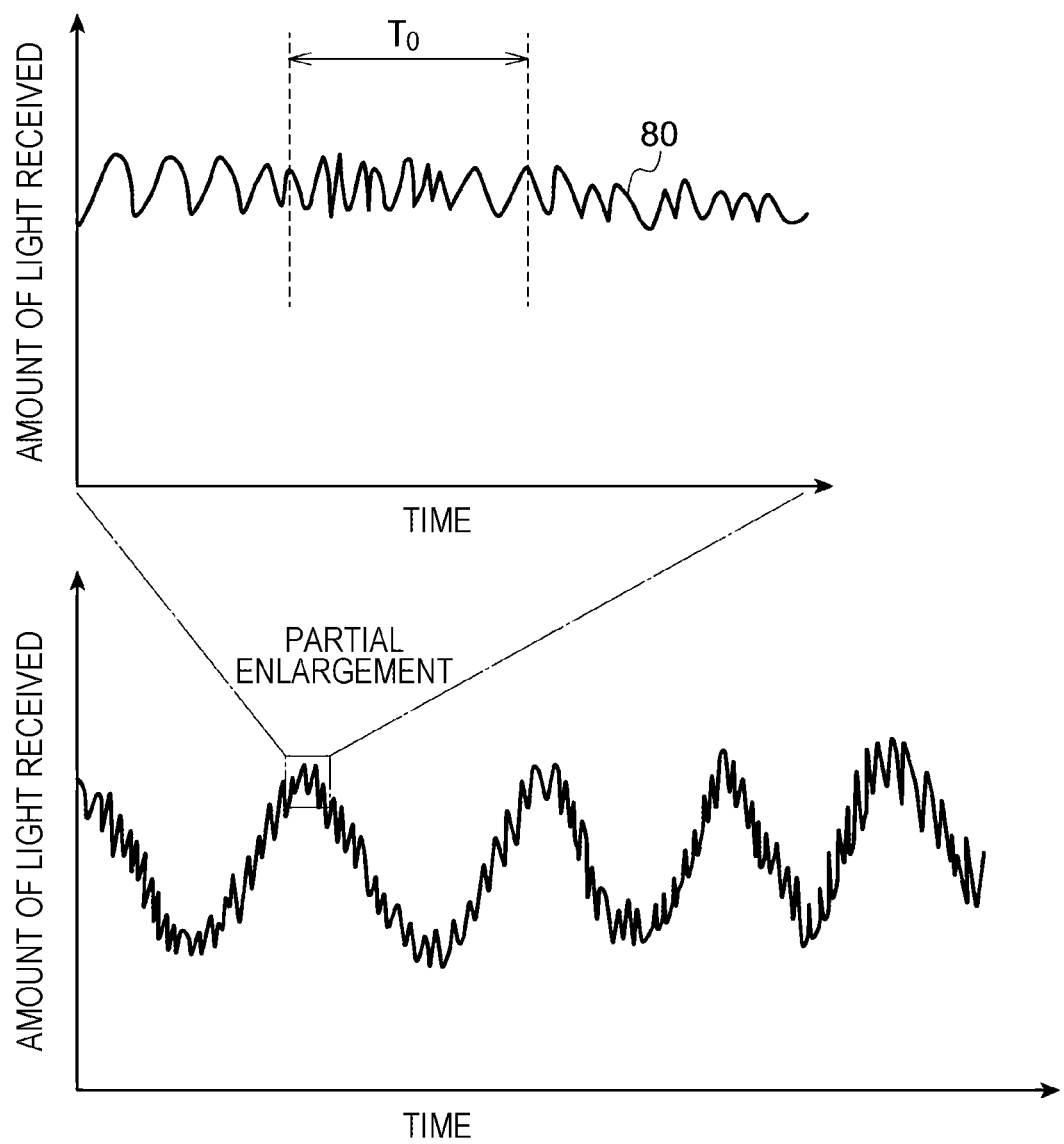
FIG. 2 is a graph illustrating one example of change in the amount of light received by reflected light from a living body according to the present exemplary embodiment.

FIG. 2 is a graph illustrating one example of change in the amount of light received by reflected light from the living body 8 according to the present exemplary embodiment.

Note that in FIG. 2, the horizontal axis of the graph 80 represents the passage of time, while the vertical axis represents the amount of light received by the light receiver 3.

As illustrated in FIG. 2, the amount of light received by the light receiver 3 changes over time, but this is thought to be because of the influence of three optical phenomena that occur when the living body 8 including blood vessels is irradiated with light.

The first optical phenomenon is thought to be a change in the absorbance of light due because a change due to pulsation in the amount of blood existing inside the blood vessels being measured. Since blood includes blood cells such as red blood cells for example and moves inside blood vessels such as the capillaries 6, changes in the amount of blood also cause the number of blood cells moving inside the blood vessels to change, and may influence the amount of light received by the light receiver 3.

The second optical phenomenon is thought to be the influence of Doppler shift.

Figure 3:
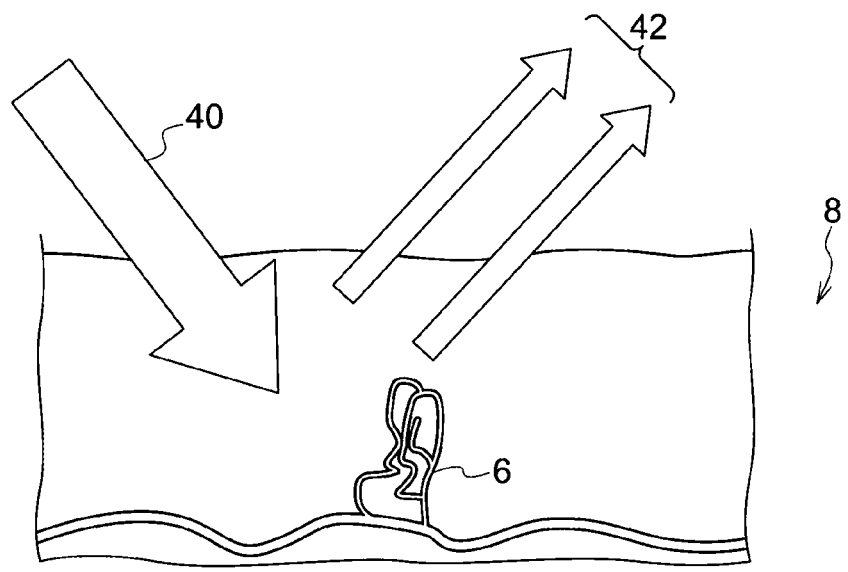
FIG. 3 is a schematic diagram accompanying a description of a Doppler shift produced in a case of irradiating a blood vessel with laser light according to the present exemplary embodiment.

FIG. 3 is a schematic diagram accompanying a description of a Doppler shift produced in a case of irradiating a blood vessel with laser light according to the present exemplary embodiment.

As illustrated in FIG. 3, for example, in the case of irradiating a region including the capillaries 6, which is one example of a blood vessel, with coherent light 40 of a frequency $\omega_0$ such as laser light from the light emitter 1, scattered light 42 scattered by blood cells moving through the capillaries 6 produces a Doppler shift having a difference frequency $\Delta\omega_0$ determined by the movement speed of the blood cells. On the other hand, the frequency of the scattered light 42 scattered by tissue (stationary tissue) such as skin that does not include moving bodies such as blood cells maintains the same frequency $\omega_0$ as the frequency of the radiated laser light. Consequently, the frequency $\omega_0+\Delta\omega_0$ of the laser light scattered by blood vessels such as the capillaries 6 and the frequency $\omega_0$ of the laser light scattered by stationary tissue interfere with each other, a beat signal having the difference frequency $\Delta\omega_0$ is observed by the light receiver 3, and the amount of light received by the light receiver 3 changes over time. Note that the difference frequency $\Delta\omega_0$ of the beat signal observed by the light receiver 3 depends on the movement speed of the blood cells, but is included in a range with an upper limit of approximately a few dozen kHz.

In addition, the third optical phenomenon is thought to be the influence of speckle.

Figure 4:
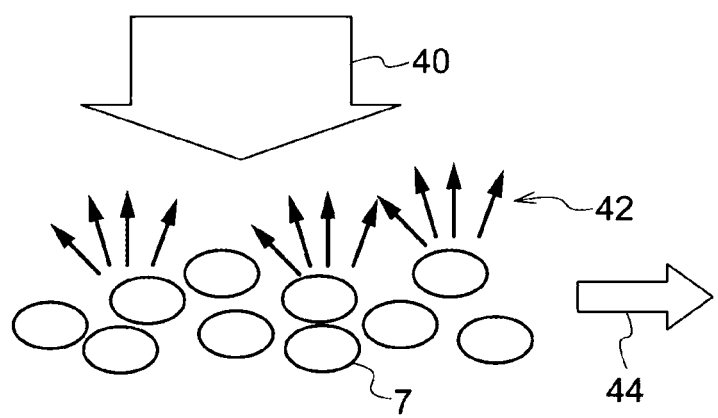
FIG. 4 is a schematic diagram accompanying a description of speckle produced in a case of irradiating a blood vessel with laser light according to the present exemplary embodiment.

FIG. 4 is a schematic diagram accompanying a description of a speckle produced in a case of irradiating a blood vessel with laser light according to the present exemplary embodiment.

As illustrated in FIG. 4, in the case of irradiating blood cells 7 such as red blood cells moving through a blood vessel in the direction of the arrow 44 with the coherent light 40 such a laser light from the light emitter 1, laser light colliding with the blood cells 7 scatters in various directions. Since the scattered light has different phases, the scattered light interferes with itself randomly. Consequently, a random light intensity distribution having a spotted pattern is produced. A distribution pattern of light intensity formed in this way is called a "speckle pattern".

As described earlier, since the blood cells 7 move inside a blood vessel, the state of light scattering in the blood cells 7 changes, and the speckle pattern fluctuates over time. Consequently, the amount of light received by the light receiver 3 changes over time.

Next, one example of obtaining blood flow information will be described. In the case of obtaining the amount of light received by the light receiver 3 over time illustrated in FIG. 2, data included in the range of a predetermined unit time $T_0$ is cut out, and by executing the fast Fourier transform (FFT) for example on the data, a spectral distribution by frequency $\omega$ is obtained.

Figure 5:
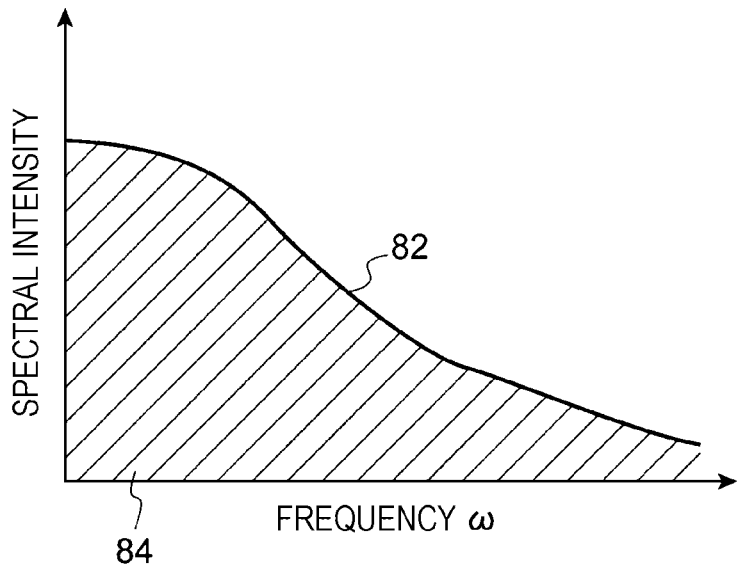
FIG. 5 is a graph illustrating one example of a spectral distribution by frequency in a unit time according to the present exemplary embodiment.

FIG. 5 is a graph illustrating one example of the spectral distribution by frequency $\omega$ in the unit time $T_0$ according to the present exemplary embodiment.

Note that in FIG. 5, the horizontal axis of the graph 82 represents the frequency $\omega$ while the vertical axis represents the spectral intensity.

Here, the amount of blood is proportional to a value obtained by standardizing the area of the power spectrum illustrated in the shaded region 84 enclosed by the horizontal axis and the vertical axis of the graph 82 by the total amount of light. Also, the blood flow speed is proportional to the average value of the frequency of the power spectrum expressed by the graph 82, and thus is proportional to the value obtained by taking the value of integrating the product of the frequency $\omega$ and the power spectrum for the frequency $\omega$ over the frequency $\omega$, and dividing the integral value by the area of the shaded region 84.

Note that since the amount of blood flow is expressed as the product of the amount of blood and the blood flow speed, it is possible to compute the amount of blood flow with a formula of the amount of blood and the blood flow speed above. The amount of blood flow, the blood flow speed, and the amount of blood are one example of blood flow information, but the blood flow information is not limited thereto.

Figure 6:
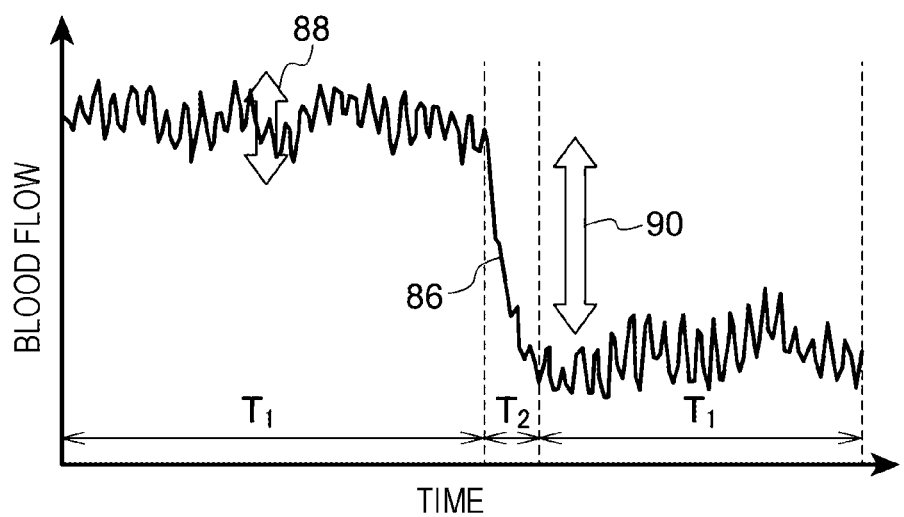
FIG. 6 is a graph illustrating one example of change in the amount of blood flow per unit time according to the present exemplary embodiment.

FIG. 6 is a graph illustrating one example of change in the amount of blood flow per unit time $T_0$ according to the present exemplary embodiment.

Note that in FIG. 6, the horizontal axis of the graph 86 represents time while the vertical axis represents the amount of blood flow.

As illustrated in FIG. 6, the amount of blood flow fluctuates with time, but the trend of fluctuation is classified into two types. For example, compared to a fluctuation range 88 of the amount of blood flow in a segment $T_1$ of FIG. 6, the fluctuation range 90 of the amount of blood flow in a segment $T_2$ is large. The reason for this is thought to be that while the change in the amount of blood flow in the segment $T_1$ is the change in the amount of blood flow mostly associated with the motion of pulsation, the change in the amount of blood flow in the segment $T_2$ indicates a change in the amount of blood flow associated with a cause such as congestion, neural activity, or the like, for example.

(Measurement of Oxygen Saturation)

Next, the measurement of oxygen saturation in the blood will be described. Oxygen saturation in the blood is one example of the blood oxygen concentration, and is an indicator indicating how much hemoglobin in the blood is bonded to oxygen. As the oxygen saturation in the blood falls, symptoms such as anemia occur more readily.

Figure 7:
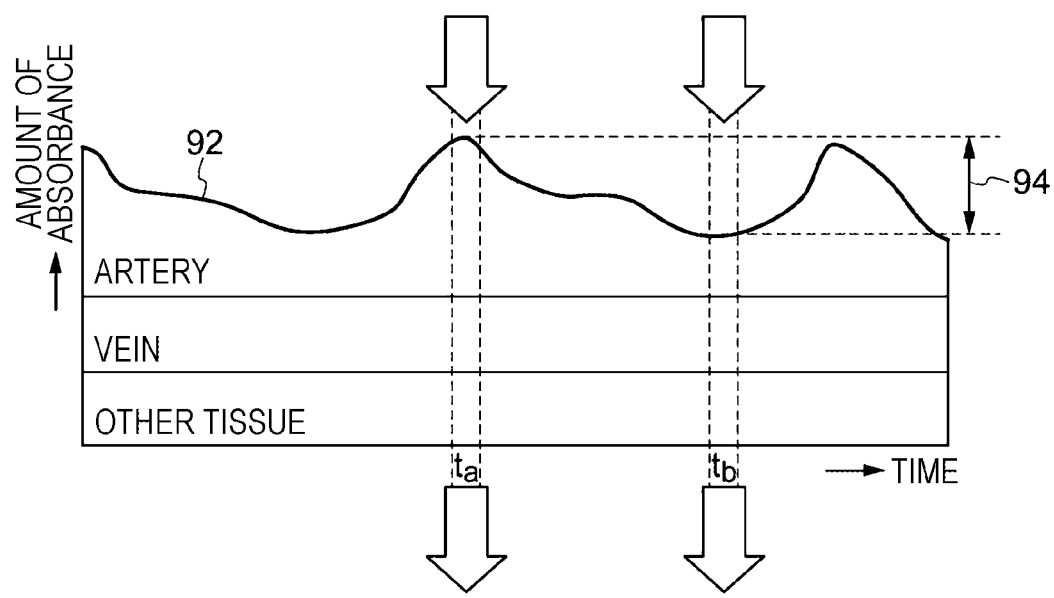
FIG. 7 is a graph illustrating one example of change in the amount of absorbance of light absorbed by a living body according to the present exemplary embodiment.

FIG. 7 is a graph illustrating one example of change in the amount of absorbance of light absorbed by the living body 8 according to the present exemplary embodiment.

Note that in FIG. 7, the horizontal axis of the graph 92 represents time while the vertical axis represents the amount of absorbance.

As illustrated in FIG. 7, the amount of absorbance in the living body 8 tends to fluctuate over time.

Further examination of the fluctuations in absorbance by the living body 8 reveals that the amount of absorbance by the arteries 4 fluctuates widely, whereas for other tissues including the veins 5 and stationary tissues, the amount of fluctuation is small enough to consider the amount of absorbance to be unchanging compared to the arteries 4. This is because since arterial blood output from the heart moves through blood vessels in association with a pulse wave, the arteries 4 expand and contract over time in the cross-sectional direction of the arteries 4, and the thickness of the arteries 4 change. Note that in FIG. 7, the range indicated by the arrow 94 denotes the amount of fluctuation in the amount of absorbance corresponding to change in the thickness of the arteries 4.

In FIG. 7, if $I_a$ is taken to be the amount of light received at a time $t_a$ and $I_b$ is taken to be the amount of light received at a time $t_b$, the amount of change ΔA in the amount of absorbance of light due to change in the thickness of the arteries 4 is expressed by Formula (1).

(Math. 1)

$$\Delta A = \ln(I_b/I_a) \qquad (1)$$

Figure 8:
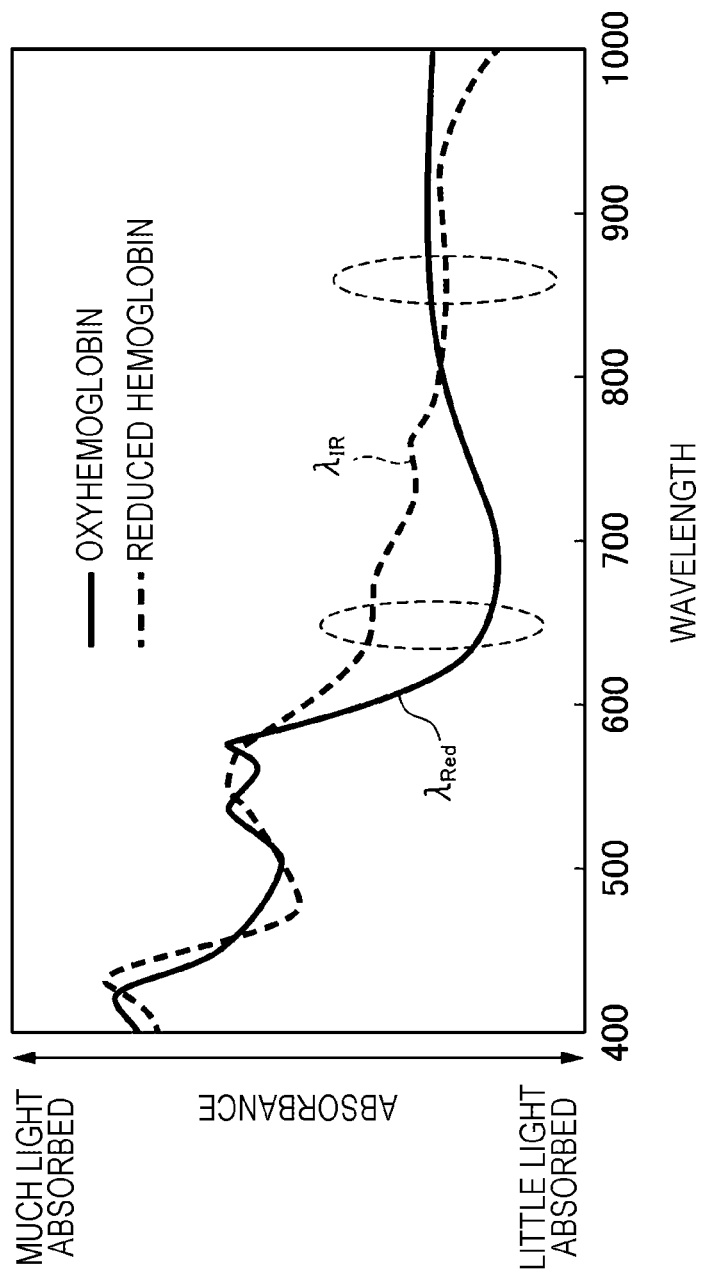
FIG. 8 is a graph illustrating one example of the absorbance characteristics by hemoglobin according to the present exemplary embodiment.

FIG. 8 is a graph illustrating one example of the absorbance characteristics by hemoglobin according to the present exemplary embodiment.

Note that in FIG. 8, the vertical axis represents absorbance while the horizontal axis represents wavelength.

As illustrated in FIG. 8, hemoglobin bonded to oxygen (oxyhemoglobin) flowing through the arteries 4 absorbs light in the infrared (IR) region having a wavelength near approximately 880 nm particularly easily, while hemoglobin not bonded to oxygen (reduced hemoglobin) absorbs light in the red region having a wavelength near approximately 665 nm particularly easily. Furthermore, the oxygen saturation exists in a proportional relationship with the ratio of the amount of change ΔA in the amount of absorbance for the different wavelengths.

Consequently, by using infrared light (IR light) and red light for which the difference in the amount of absorbance by oxyhemoglobin and reduced hemoglobin is more apparent compared to combinations of other wavelengths, and computing each of the ratios of the amount of change $\Delta A_{IR}$ in the amount of absorbance in the case of irradiating the living body 8 with IR light and the amount of change $\Delta A_{Red}$ in the amount of absorbance in the case of irradiating the living body 8 with red light, the oxygen saturation S is computed according to Formula (2). Note that in Formula (2), k is a constant of proportionality.

(Math. 2)

$$S = k(\Delta A_{Red}/\Delta A_{IR}) \qquad (2)$$

In other words, in the case of computing the oxygen saturation in the blood, multiple light emitters 1 that radiate light of different wavelengths, or more specifically, a light emitter 1 that radiates IR light and a light emitter 1 that radiates red light may have partially overlapping light emission periods, but desirably are made to emit light without having overlapping light emission periods. Additionally, the reflected light or transmitted light from each of the light emitters 1 is received by the light receiver 3, and by computing Formula (1) and Formula (2) or a publicly available formula obtained by transforming these formulas from the amount of light received at each point in time of light reception, the oxygen saturation is measured.

As the publicly available formula obtained by transforming Formula (1) above, Formula (1) may be expanded to express the amount of change ΔA in the amount of absorbance of light as in Formula (3), for example.

(Math. 3)

$$\Delta A = \ln I_b - \ln I_a \qquad (3)$$

Also, Formula (1) may be transformed as in Formula (4).

(Math. 4)

$$\Delta A = \ln(I_b/I_a) = \ln(1+(I_b-I_a)/I_a) \qquad (4)$$

Normally, since $(I_b-I_a) \ll I_a$, the relationship $\ln(I_b/I_a) \approx (I_b-I_a)/I_a$ holds, and thus instead of Formula (1), Formula (5) may be used as the amount of change ΔA in the amount of absorbance of light.

(Math. 5)

$$\Delta A \approx (I_b-I_a)/I_a \qquad (5)$$

Note that in the following, when distinguishing the light emitter 1 that radiates IR light from the light emitter 1 that radiates red light, the light emitter 1 that radiates IR light will be designated the "light emitter LD1" while the light emitter 1 that radiates red light will be designated the "light emitter LD2". Also, as an example, the light emitter LD1 is taken to be the light emitter 1 used to compute the amount of blood flow, while the light emitter LD1 and the light emitter LD2 are taken to be the light emitters 1 used to compute the oxygen saturation in the blood.

Also, in the case of measuring the oxygen saturation in the blood, since it is sufficient for the frequency of measuring the amount of light received to be approximately from 30 Hz to 1000 Hz, it is also sufficient for the light emission frequency that expresses the number of flashes per second by the light emitter LD2 to be approximately from 30 Hz to 1000 Hz. Consequently, from the perspective of power consumption and the like in the light emitter LD2, it is desirable to set the light emission frequency of the light emitter LD2 lower than the light emission frequency of the light emitter LD1, but the light emission frequency of the light emitter LD2 may also be matched to the light emission frequency of the light emitter LD1 to make the light emitter LD1 and the light emitter LD2 emit light in alternation.

Figure 9:
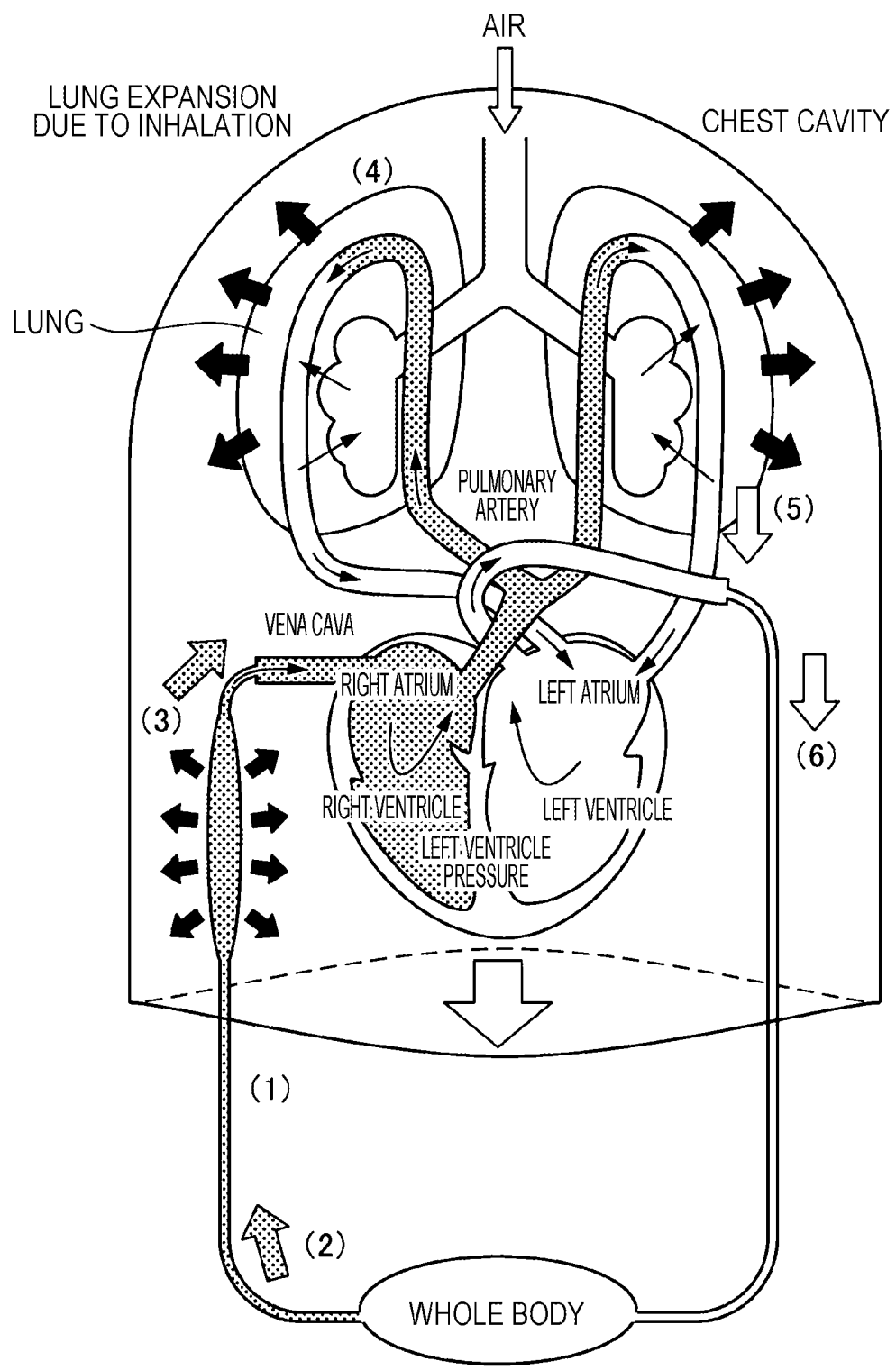
FIG. 9 is a schematic diagram accompanying a description of the principle of measuring a respiration waveform according to the present exemplary embodiment.

Next, FIG. 9 will be referenced to describe the principle of measuring a respiration waveform from a pulse wave signal obtained from a peripheral site on the living body 8. Examples of the peripheral site referred to herein include the tips of the fingers, the tips of the toes, the earlobes, and the like. Note that the peripheral site also includes sites past the elbow, sites past the knee, and the like. In addition, the respiration waveform is the waveform of a signal indicating the respiratory state of the living body 8, and is taken to be the waveform of a time-series signal expressing change over time in exhalation and inhalation.

FIG. 9 is a schematic diagram accompanying a description of the principle of measuring the respiration waveform according to the present exemplary embodiment.

As illustrated in FIG. 9, during respiration, the amplitude of the pulse wave signal decreases according to the steps indicated below. (S1) The intrathoracic pressure falls to a negative pressure, and the lungs expand.
(S2) The amount of venous return increases.
(S3) The amount of blood flowing into the right atrium increases.
(S4) The vascular bed of the lungs expands, and the amount of blood retained by the lungs increases.
(S5) The amount of blood returning to the left atrium from the lungs decreases.
(S6) The stroke volume of the left ventricle decreases.
(S7) The amplitude of the pulse wave decreases.

On the other hand, during respiration, the amplitude of the pulse wave signal increases according to the steps indicated below.
(S8) Blood squeezed out from the lungs flows into the left ventricle.

(S9) The amplitude of the pulse wave increases.

In other words, since the influence of the "pump action of the lungs" caused by respiration is superimposed onto the pulsation caused by the "pump action of the heart", it is possible to measure the respiration waveform from a pulse wave signal obtained from a peripheral site of the living body 8.

Figure 10:
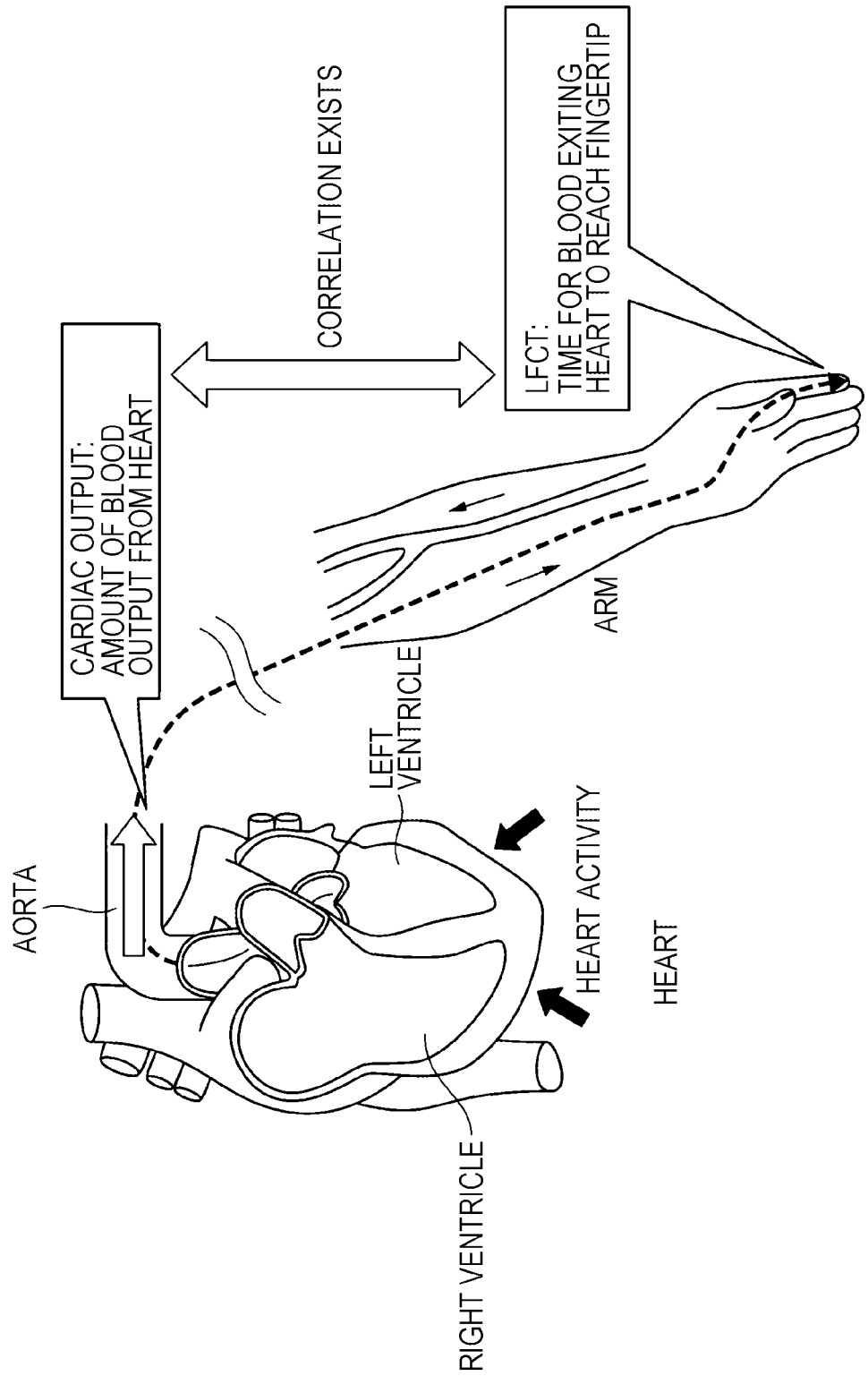
FIG. 10 is a schematic diagram accompanying a description of the principle of measuring output according to the present exemplary embodiment.

Next, FIG. 10 will be referenced to describe a principle of measuring the lung to finger circulation time (LFCT), which is one example of an indicator correlated with the output of blood from the heart. The output referred to herein is not limited to the cardiac output described earlier, and also includes stroke volume, cardiac index, and the like. Note that the cardiac output is defined as the amount of blood output to the arteries by contraction of the heart per unit time (for example, per minute). The stroke volume is defined as the amount of blood output to the arteries by a single contraction of the heart. The cardiac index is defined as a coefficient obtained by dividing the cardiac output by the body surface area of the test subject. Also, the LFCT is defined as the time for oxygen taken in by respiration to pass through the lungs and heart, and reach a fingertip.

FIG. 10 is a schematic diagram accompanying a description of the principle of measuring the output according to the present exemplary embodiment.

As illustrated in FIG. 10, the above output and the LFCT are correlated. For example, if CO is taken to be the cardiac output as one example of the output, the cardiac output CO is computed according to Formula (6) indicated below.

(Math. 6)

$$CO = (a_0 \times S)/\text{LFCT} \tag{6}$$

Herein, $a_0$ is a constant. For example, $a_0 = 50$ is used. Also, S is the body surface area (m²) of the test subject, and the units of the LFCT are seconds.

Figure 11:
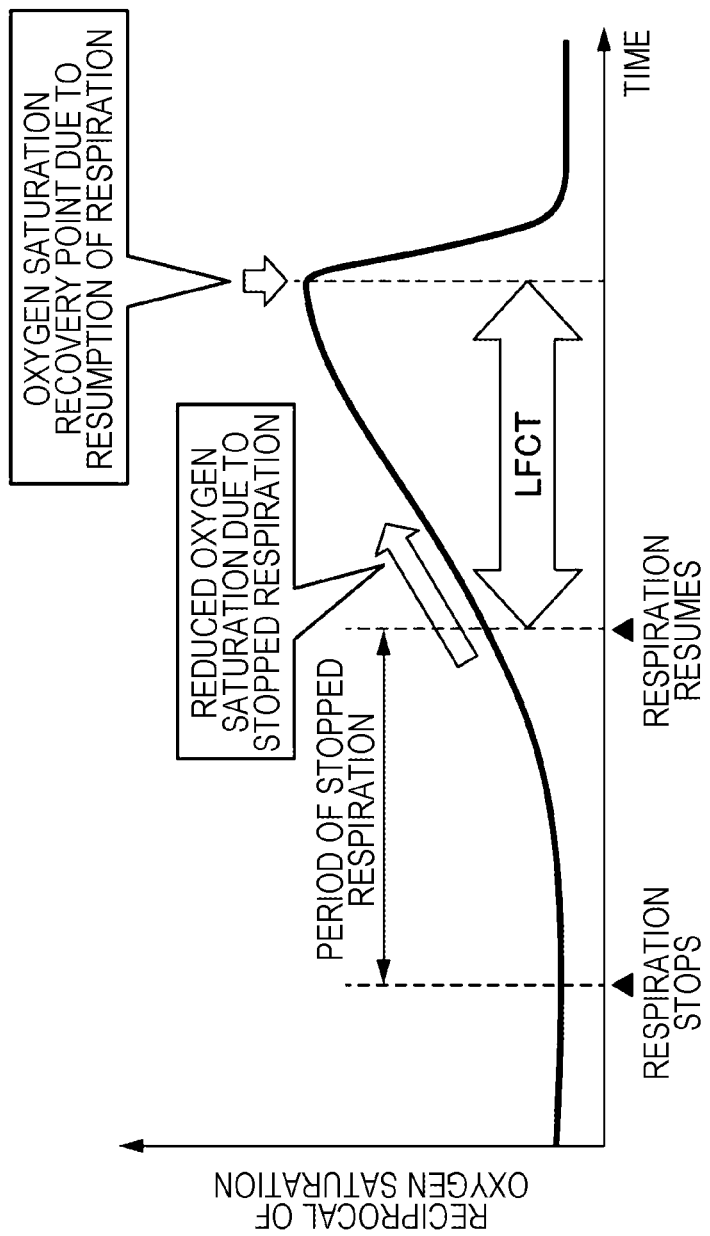
FIG. 11 is a graph for explaining one example of a method of measuring the LFCT according to the present exemplary embodiment.

FIG. 11 is a graph for explaining one example of a method of measuring the LFCT according to the present exemplary embodiment.

Note that in FIG. 11, the vertical axis represents the reciprocal of the oxygen saturation while the horizontal axis represents time.

As illustrated in FIG. 11, the LFCT according to the present exemplary embodiment is measured from the change in the oxygen saturation described above. In other words, the LFCT is obtained by measuring the amount of time from the point in time at which respiration resumes after stopping respiration for a fixed period, until the inflection point that indicates that the oxygen saturation has recovered.

Meanwhile, in the above LFCT measurement, to detect the change in the blood oxygen concentration, as one example, the ratio of the amount of change in the IR light signal and the amount of change in the red light signal, or in other words, the amplitude ratio of two pulse wave signals of different wavelengths (herein, the IR light signal and the red light signal) is used. In the case of using the amplitude ratio, for example, for a living body having an atrial fibrillation, a living body with reduced blood flow due to the influence of factors such as environmental temperature and mental state, and the like, accurately measuring the blood oxygen concentration may be difficult in some situations.

The following describes a biological information measurement device that measures the blood oxygen concentration accurately, even for a living body having an atrial fibrillation, a living body with reduced blood flow due to the influence of factors such as environmental temperature and mental state, and the like.

Figure 12:
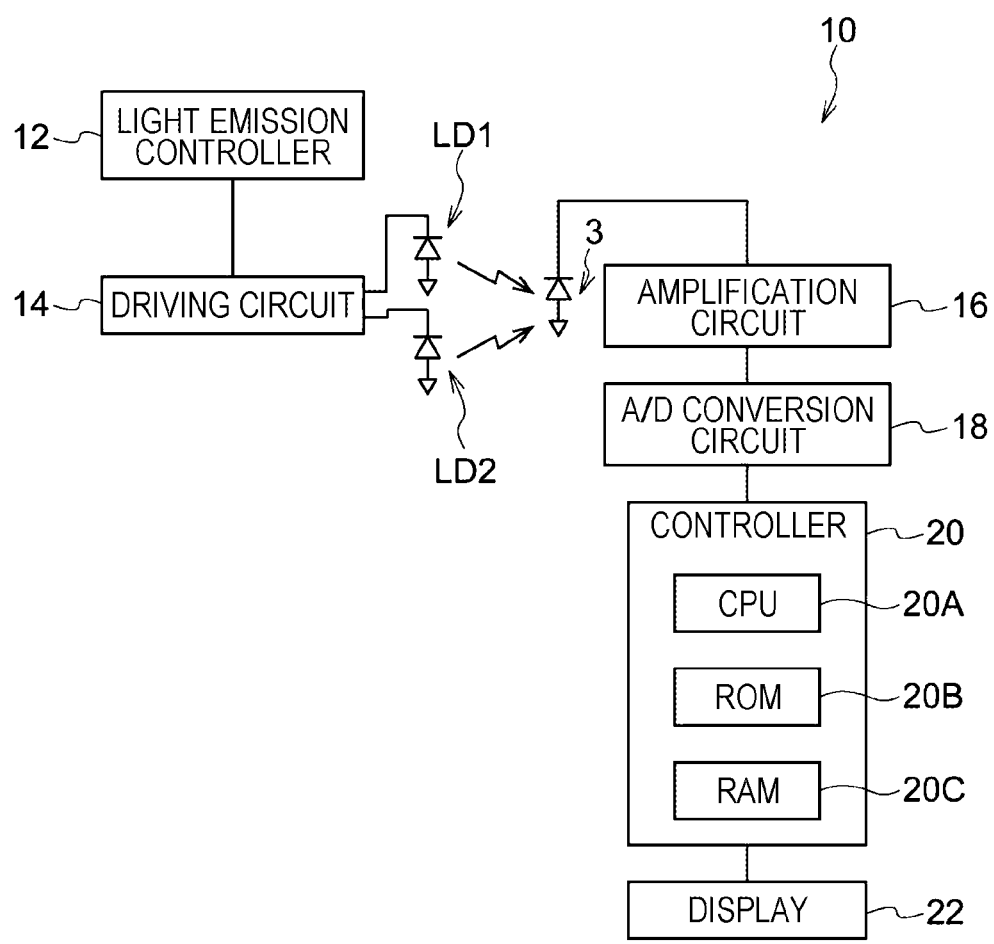
FIG. 12 is a block diagram illustrating one example of an electrical configuration of the biological information measurement device according to the present exemplary embodiment.

FIG. 12 is a block diagram illustrating one example of an electrical configuration of a biological information measurement device 10 according to the present exemplary embodiment.

As illustrated in FIG. 12, the biological information measurement device 10 according to the present exemplary embodiment is provided with a light emission controller 12, a driving circuit 14, an amplification circuit 16, an analog/digital (A/D) conversion circuit 18, a controller 20, a display 22, the light emitter LD1, the light emitter LD2, and the light receiver 3. Note that the light emitter LD1, the light emitter LD2, the light receiver 3, and the amplification circuit 16 form a sensor unit. Also, the light emission controller 12, the driving circuit 14, the amplification circuit 16, the A/D conversion circuit 18, the controller 20, and the display 22 form a main unit. In the present exemplary embodiment, the sensor unit and the main unit are configured as separate units able to communicate in a wired or wireless manner. However, the sensor unit and the main unit may also be configured in a unified manner. Also, the sensor unit is attached to adhere closely to the living body 8 such that external light is not input. As one example, the sensor unit according to the present exemplary embodiment is attached to a fingertip of the living body 8, but is also attachable to another peripheral site such as an earlobe.

The light emission controller 12 outputs a control signal that controls the light emission cycle and the light emission period of the light emitter LD1 and the light emitter LD2 to the driving circuit 14 including a power supply circuit that supplies driving power to the light emitter LD1 and the light emitter LD2. Note that the light emission controller 12 may also be realized as part of the controller 20.

The driving circuit 14 receives the control signal from the light emission controller 12, and following the light emission cycle and light emission period indicated by the control signal, supplies driving power to the light emitter LD1 and the light emitter LD2, and drives the light emitter LD1 and the light emitter LD2.

The light receiver 3 is one example of a light receiving unit, receiving light of a first wavelength from the light emitter LD1 and outputting a first received light signal corresponding to the received light of the first wavelength, and also receiving light of a second wavelength from the light emitter LD2 and outputting a second received light signal corresponding to the received light of the second wavelength. Note that in the present exemplary embodiment, a range of wavelengths corresponding to the infrared region is applied as the first wavelength, and a range of wavelengths corresponding to the red region is applied as the second wavelength. Also, an IR light signal is applied as the first received light signal, and a red light signal is applied as the second received light signal.

The amplification circuit 16 converts a current depending on the light intensity and produced by the light receiver 3 into a voltage, and amplifies the voltage to a voltage level prescribed as the input voltage range of the A/D conversion circuit 18.

The A/D conversion circuit 18 receives the voltage amplified by the amplification circuit 16 as input, and outputs an amount of light received by the light receiver 3 expressed by the magnitude of the voltage as a numerical value.

The controller 20 is provided with a central processing unit (CPU) 20A, read-only memory (ROM) 20B, and random access memory (RAM) 20C. The ROM 20B stores the biological information measurement program. The biological information measurement program may be preinstalled in the biological information measurement device 10, for example. The biological information measurement program may also be realized by being stored on a non-volatile storage medium or distributed over a network, and installed appropriately in the biological information measurement device 10. Note that anticipated examples of the non-volatile storage medium include a Compact Disc-Read-Only Memory (CD-ROM), a magneto-optical disc, an HDD, a Digital Versatile Disc-Read-Only Memory (DVD-ROM), flash memory, a memory card, and the like.

The display 22 is one example of a notification unit that presents a notification of the result of measuring biological information. For the display 22, for example, a liquid crystal display (LCD), an organic electroluminescence (EL) display, or the like is used. The display 22 includes an integrated touch panel.

Figure 13:
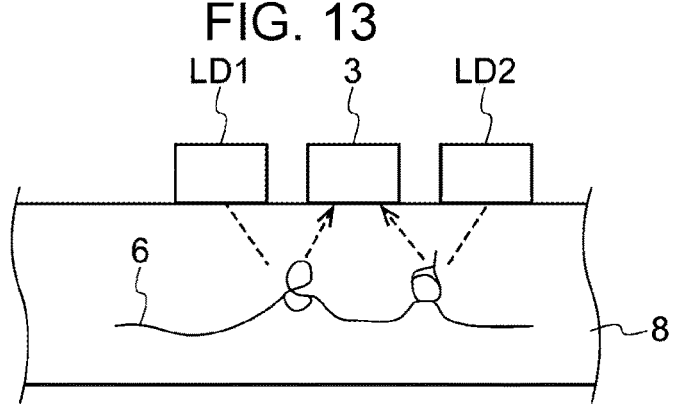
FIG. 13 is a diagram illustrating one example of an arrangement of light emitters and a light receiver in the biological information measurement device according to the present exemplary embodiment.
Figure 14:
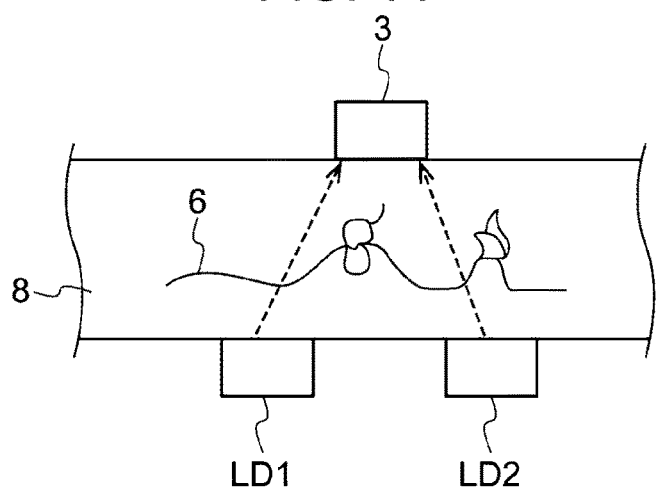
FIG. 14 is a diagram illustrating another example of an arrangement of light emitters and a light receiver in the biological information measurement device according to the present exemplary embodiment.

FIG. 13 is a diagram illustrating one example of an arrangement of the light emitter LD1, the light emitter LD2, and the light receiver 3 in the biological information measurement device 10 according to the present exemplary embodiment. Also, FIG. 14 is a diagram illustrating a different example of an arrangement of the light emitter LD1, the light emitter LD2, and the light receiver 3 in the biological information measurement device 10 according to the present exemplary embodiment.

As illustrated in FIG. 13, the light emitter LD1, the light emitter LD2, and the light receiver 3 are arranged side by side facing one side of the living body 8. In this case, the light receiver 3 receives light from the light emitter LD1 and the light emitter LD2 that has been transmitted near the surface of the living body 8.

Note that the arrangement of the light emitter LD1, the light emitter LD2, and the light receiver 3 is not limited to the example arrangement of FIG. 13. For example, as illustrated in FIG. 14, the light emitter LD1, the light emitter LD2, and the light receiver 3 may also be arranged at opposing positions with the living body 8 interposed in between. In this case, the light receiver 3 receives light from the light emitter LD1 and the light emitter LD2 that has been transmitted through the living body 8.

Note that herein, as one example, the light emitter LD1 and the light emitter LD2 both are described as being surface-emitting laser elements, but the light emitter LD1 and the light emitter LD2 are not limited thereto, and may also be edge-emitting laser elements. Also, the light radiated from each of the light emitter LD1 and the light emitter LD2 does not have to be laser light. In this case, a light-emitting diode (LED) or an organic light-emitting diode (OLED) may be used for each of the light emitter LD1 and the light emitter LD2.

Figure 15:
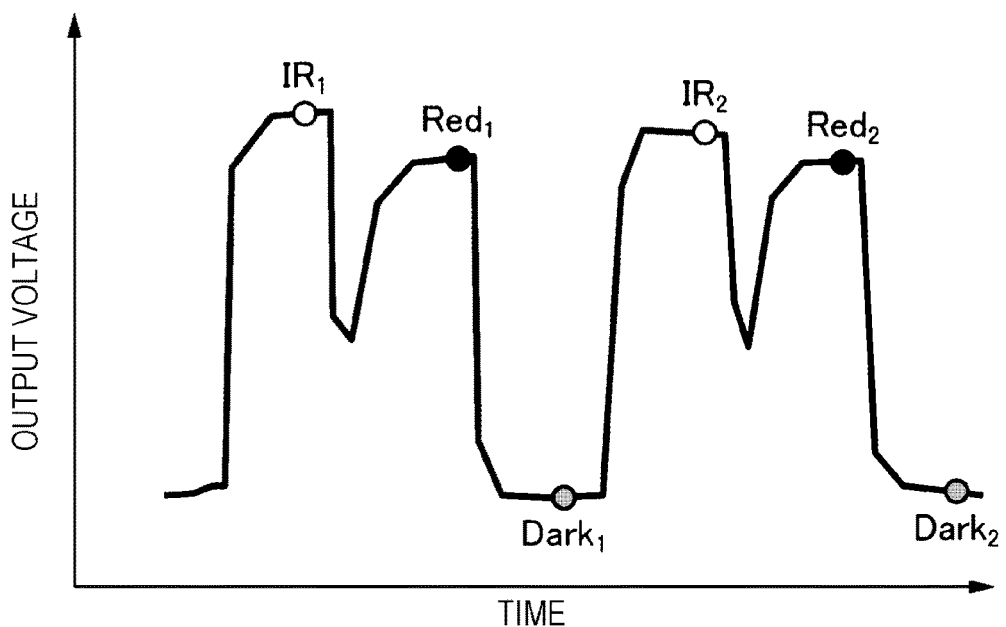
FIG. 15 is a graph illustrating one example of the sampling timing of data in a light receiver according to the present exemplary embodiment.

FIG. 15 is a graph illustrating one example of the sampling timing of data in the light receiver 3 according to the present exemplary embodiment. In FIG. 15, the positions of the circle marks indicate the sampling timings.

Note that in FIG. 15, the vertical axis represents the output voltage of the light receiver 3 while the horizontal axis represents time.

As illustrated in FIG. 15, in the case of treating $IR_1$, $IR_2$, ..., $IR_n$ as output voltages corresponding to the light that the light receiver 3 receives from the light emitter LD1, $IR(t)=IR_1, ..., IR_n$ is obtained as time series data. Similarly, in the case of treating $Red_1$, $Red_2$, ..., $Red_n$ as output voltages corresponding to the light that the light receiver 3 receives from the light emitter LD2, $Red(t)=Red_1$, $Red_2$, ..., $Red_n$ is obtained as time series data. At this time, periods during which neither of the light emitter LD1 and the light emitter LD2 emit light may also be provided, and outputs $Dark_1$, $Dark_2$, ..., $Dark_n$ may be obtained in these dark states. In this case, IR(t) may also be taken to be $IR_1-Dark_1$, $IR_2-Dark_2$, $IR_n-Dark_n$. Similarly, Red(t) may also be taken to be $Red_1-Dark_1$, $Red_2-Dark_2$, ..., $Red_n-Dark_n$. It is desirable for the above data to be sampled in near the end of each light emission period in a state of stable output.

Figure 16:
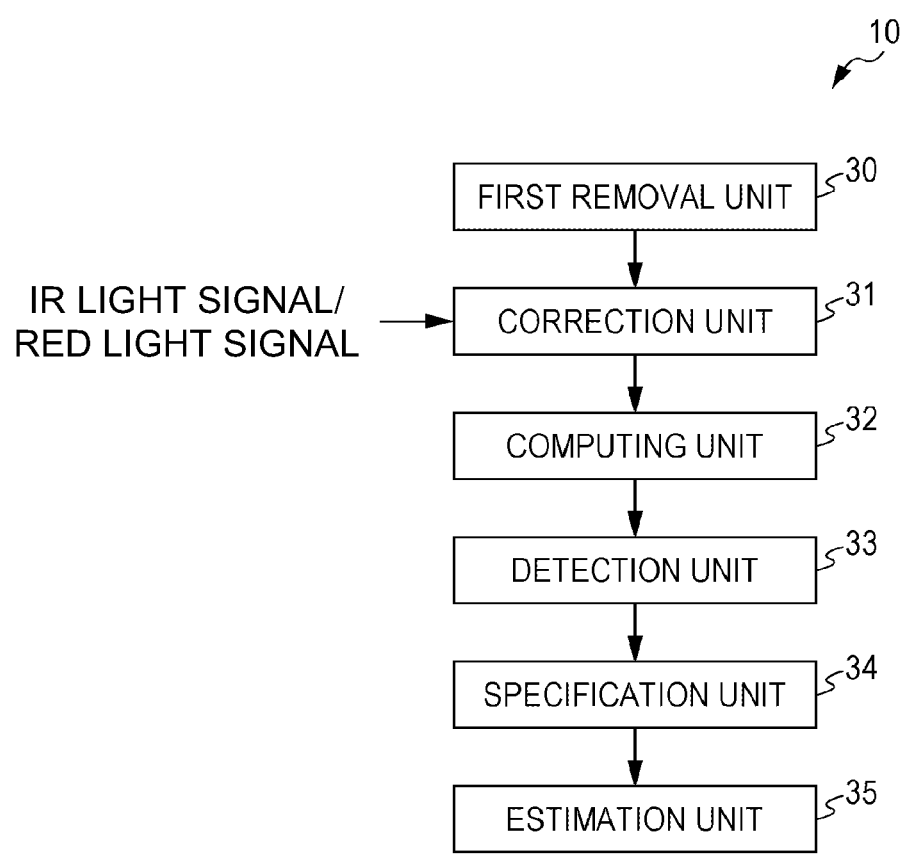
FIG. 16 is a block diagram illustrating one example of a functional configuration of the biological information measurement device according to a first exemplary embodiment.

The CPU 20A of the biological information measurement device 10 according to the present exemplary embodiment loads the biological information measurement program stored in the ROM 20B into the RAM 20C and executes the program, and thereby functions as each unit illustrated in FIG. 16.

FIG. 16 is a block diagram illustrating one example of a functional configuration of the biological information measurement device 10 according to a first exemplary embodiment.

As illustrated in FIG. 16, the CPU 20A of the biological information measurement device 10 according to the present exemplary embodiment functions as a first removal unit 30, a correction unit 31, a computing unit 32, a detection unit 33, a specification unit 34, and an estimation unit 35. Note that the first removal unit 30 is not a required component, and it is sufficient to provide the first removal unit 30 only when appropriate.

First, the configuration of each unit in the case of not providing the first removal unit 30 will be described.

The correction unit 31 according to the present exemplary embodiment receives each of the IR light signal and the red light signal output from the light receiver 3, and corrects the IR light signal to reduce the difference between the amount of change in the IR light signal (hereinafter designated ΔIR) and the amount of change in the red light signal (hereinafter designated ΔRed) associated with change in the amount of arterial blood in the living body 8. The change in the amount of arterial blood expresses the amplitude of pulsation associated with heartbeat. Note that in this case, the IR light signal is treated as an example of the first signal, and the red light signal is treated as an example of the second signal.

It is desirable for the above correction to make ΔIR and ΔRed equal. Herein, ΔIR is expressed as the amplitude of the IR light signal, and ΔRed is expressed as the amplitude of the red light signal. In this case, the above correction is performed by multiplying the values of the IR light signal (IR(t)) by a coefficient α representing the amplitude ratio of ΔIR and ΔRed (ΔRed/ΔIR). In other words, the corrected output of IR(t) becomes α×IR(t).

The computing unit 32 according to the present exemplary embodiment computes the change in the blood oxygen concentration in the living body 8 on the basis of the IR light signal and the red light signal corrected by the correction unit 31. As one example, the change in the blood oxygen concentration is expressed as the difference between the IR light signal and the red light signal corrected by the correction unit 31 (hereinafter, this difference is designated the "pulse wave difference"). For example, if β(t) is taken to be the pulse wave difference, β(t) is computed according to Formula (7) indicated below.

(Math. 7)

$$\beta(t)=\alpha \times IR(t)-Red(t) \qquad (7)$$

The detection unit 33 according to the present exemplary embodiment detects the inflection point of the blood oxygen concentration associated with a change in the amount of oxygen inhaled by the living body 8 on the basis of the pulse wave difference β(t) computed by the computing unit 32. Note that one example of a method for causing the amount of inhaled oxygen to change is the method of holding one's breath and the like. Also, the change in the amount of inhaled oxygen referred to herein is assumed to be a change that induces a change in the blood oxygen concentration for at least several seconds, and does not include slight changes due to a normal respiratory state (for example, inhaling and exhaling at an ordinary rate and an ordinary depth). In other words, in the normal respiratory state, it is determined that there is no change in the amount of inhaled oxygen, whereas in the case of causing a change from the normal respiratory state by holding one's breath, taking shallow breaths, inhaling gas with a high oxygen concentration, or the like, it is determined that the amount of inhaled oxygen has changed.

The specification unit 34 according to the present exemplary embodiment specifies the amount of time from the point in time at which the amount of oxygen inhaled by the living body 8 changes until the inflection point in the blood oxygen concentration detected by the detection unit 33. Note that the point in time at which the amount of inhaled oxygen changes is, for example, the point in time at which the test subject resumes breathing after a state of holding one's breath or the like. In the present exemplary embodiment, the time specified by the specification unit 34 is taken to be the LFCT.

The estimation unit 35 according to the present exemplary embodiment estimates the output from the LFCT specified by the specification unit 34. For example, Formula (6) above is used to estimate the cardiac output, which is one example of output.

At this point, each of the IR light signal and the red light signal includes a component expressing change in the amount of blood due to pulsation, neural activity, and the like, and a component expressing change in the oxygen concentration due to the change in the amount of inhaled oxygen. Additionally, according to the above pulse wave difference $\beta(t)$, by multiplying IR(t) by the coefficient $\alpha(=\Delta Red/\Delta IR)$ and adopting the difference between $\alpha \times IR(t)$ and a Red(t), the components expressing the change in the amount of arterial blood are canceled out, and only the components expressing the change in the oxygen concentration are extracted.

Note that in the above, the coefficient $\alpha$ is taken to be $(\Delta Red/\Delta IR)$ to correct the IR light signal, but the coefficient $\alpha$ may also be taken to be $(\Delta IR/\Delta Red)$ to correct the red light signal. In this case, the pulse wave difference $\beta(t)$ is computed according to Formula (8) indicated below.

(Math. 8)

$$\beta(t) = IR(t) - \alpha \times Red(t) \quad (8)$$

Also, the above describes the case of correcting either one of the IR light signal or the red light signal, which are one example of two pulse wave signals, but both the IR light signal and the red light signal may also be corrected. Also, in the above, the red light signal is subtracted from the IR light signal, but the IR light signal may also be subtracted from the red light signal. In this case, the direction of the inflection point appearing in $\beta(t)$ is different.

Herein, the pulse wave signal when computing the coefficient $\alpha$ and the pulse wave signal to which the computed coefficient $\alpha$ is applied are shifted in time. In other words, the above correction is applied by multiplying the coefficient $\alpha$ representing the amplitude ratio of $\Delta IR$ and $\Delta Red$ before causing the amount of inhaled oxygen to change by IR(t) or Red(t) after causing the amount of inhaled oxygen to change. For example, it is desirable to use a pulse wave signal when the test subject is resting before holding one's breath as the pulse wave signal to use when computing the coefficient $\alpha$.

Next, the configuration of each unit in the case of providing the first removal unit 30 will be described.

The first removal unit 30 according to the present exemplary embodiment removes the DC component from each of the IR light signal and the red light signal output from the light receiver 3, and outputs each of the IR light signal and the red light signal with the DC component removed to the correction unit 31. As one example, a high-pass filter or a band-pass filter is applied as the first removal unit 30. Note that in this case, the IR light signal with the DC component removed by the first removal unit 30 is treated as the first signal, and the red light signal with the DC component removed by the first removal unit 30 is treated as the second signal.

The correction unit 31 receives the IR light signal and the red light signal with the DC component removed by the first removal unit 30, and derives the coefficient $\alpha$ representing the amplitude ratio between the amplitude of the received IR light signal and the amplitude of the received red light signal. After that, the correction unit 31 performs correction by multiplying IR(t), which are the values of the IR light signal, or Red(t), which are the values of the red light signal, received from the light receiver 3 without going through the first removal unit 30 by the coefficient $\alpha$ derived above. Note that since the computing unit 32, the detection unit 33, the specification unit 34, and the estimation unit 35 are similar, a repeated description will be omitted.

At this point, as an exemplary modification of the biological information measurement device 10 illustrated in FIG. 16, a configuration not provided with the computing unit 32 is also acceptable. In this case, after the amount of oxygen inhaled by the living body 8 changes, the detection unit 33 detects the inflection point in the blood oxygen concentration obtained from the IR light signal and the red light signal of which at least one has been corrected by the correction unit 31.

Figure 17:
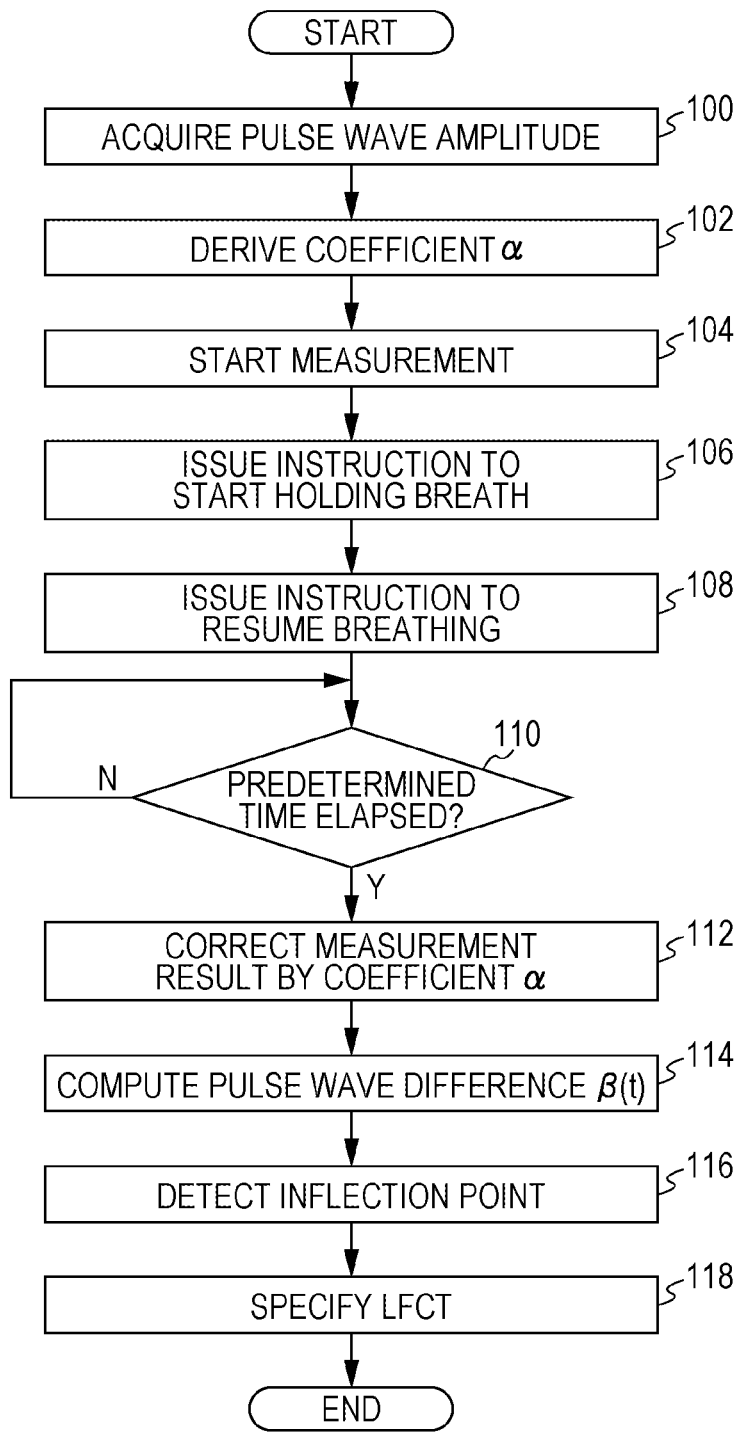
FIG. 17 is a flowchart illustrating one example of the flow of the process of a biological information measurement program according to the first exemplary embodiment.

Next, FIG. 17 will be referenced to describe the action of the biological information measurement device 10 according to the first exemplary embodiment. Note that FIG. 17 is a flowchart illustrating one example of the flow of the process of the biological information measurement program according to the first exemplary embodiment.

First, when the biological information measurement device 10 is powered on by an operation by the test subject or a measurement technician, the biological information measurement program is launched, and each of the following steps is executed.

In step 100 of FIG. 17, the correction unit 31 acquires the amplitude ($\Delta IR$) of the IR light signal obtained from the light receiver 3, and acquires the amplitude ($\Delta Red$) of the red light signal obtained from the light receiver 3. In this step 100, first, each of $\Delta IR$ and $\Delta Red$ is acquired as a pulse wave amplitude while the test subject remains in a resting state.

Figure 18:
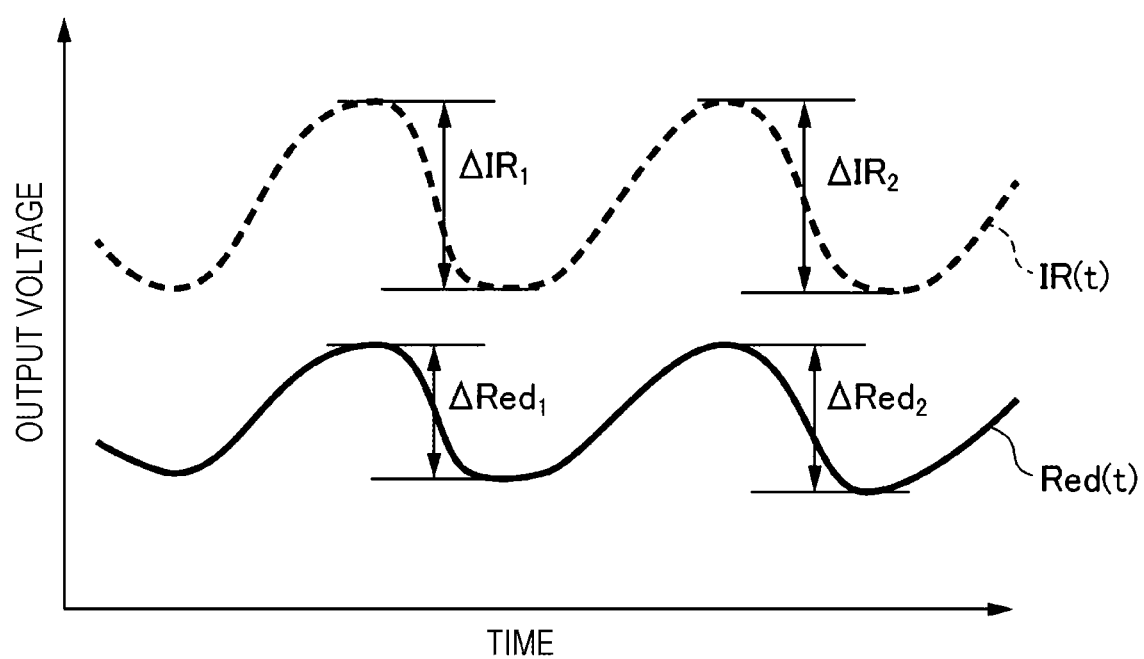
FIG. 18 is a graph illustrating one example of the amplitude of an IR light signal and the amplitude of a red light signal according to the present exemplary embodiment.

FIG. 18 is a graph illustrating one example of the amplitude of the IR light signal and the amplitude of the red light signal according to the present exemplary embodiment.

Note that in FIG. 18, the vertical axis represents the output voltage of the light receiver 3 while the horizontal axis represents time.

As illustrated in FIG. 18, the correction unit 31 acquires $\Delta IR$ from IR(t), which is the time series data of the values of the IR light signal, and acquires $\Delta Red$ from Red(t), which is the time series data of the values of the red light signal.

In step 102, the correction unit 31 derives the coefficient α representing the amplitude ratio of ΔIR and ΔRed on the basis of ΔIR and ΔRed acquired in step 100. As an example, the coefficient α is derived according to one of the methods indicated below.

(a) The amplitude ratio obtained at any timing is adopted. Note that in this case, the timing may also be after the start of the LFCT measurement.

Figure 19:
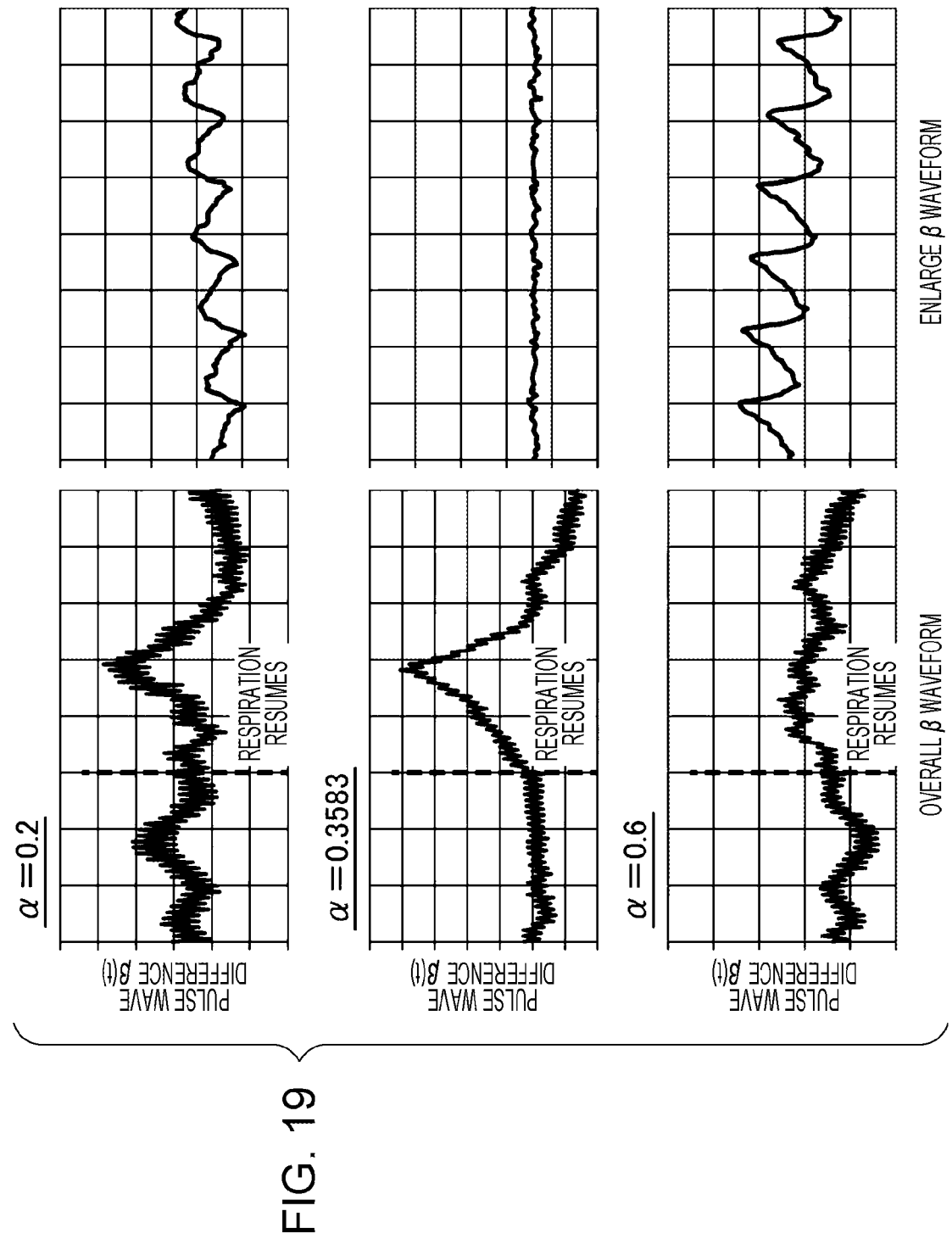
FIG. 19 is a graph illustrating one example of the relationship between a coefficient and a pulse wave difference according to the present exemplary embodiment.

(b) The average value of multiple amplitude ratios obtained in a fixed period is adopted. In the case of this method, a coefficient α that is suited to measurement is computed compared to the case of deriving the coefficient α by adopting the amplitude ratio at only a single point. (c) After measurement ends, the coefficient α is varied between 0 and 1 as illustrated in FIG. 19 for example, and the value with the smallest frequency component of pulsation appearing in the pulse wave difference β(t) is adopted. However, in the case of taking the coefficient α to be (ΔRed/ΔIR), the condition ΔIR>ΔRed is assumed to be satisfied. In the case of this method, it is not necessary to derive the coefficient α during measurement, and thus the measurement time is shortened, for example.

FIG. 19 is a graph illustrating one example of the relationship between the coefficient α and the pulse wave difference β(t) according to the present exemplary embodiment.

Note that in FIG. 19, the vertical axis represents the pulse wave difference β(t). Also, in this example, α=ΔRed/ΔIR and β(t)=α×IR(t)−Red(t).

The upper part in FIG. 19 illustrates an overall waveform and an enlarged waveform of the pulse wave difference β(t) for the case in which the coefficient α=0.2. The diagram on the left is the overall waveform, while the diagram on the right is the enlarged waveform.

The middle part in FIG. 19 illustrates an overall waveform and an enlarged waveform of the pulse wave difference β(t) for the case in which the coefficient α=0.3583. The diagram on the left is the overall waveform, while the diagram on the right is the enlarged waveform.

The lower part in FIG. 19 illustrates an overall waveform and an enlarged waveform of the pulse wave difference β(t) for the case in which the coefficient α=0.6. The diagram on the left is the overall waveform, while the diagram on the right is the enlarged waveform.

As the above demonstrates, in the case in which the coefficient α=0.3583, the frequency component of pulsation appearing in the pulse wave difference β(t) is minimized. Consequently, according to the method of (c) above, the coefficient α=0.3583 is adopted, and the pulse wave difference β(t) in which the inflection point of oxygen concentration is at a correct position is obtained.

In step 104, the correction unit 31 receives an instruction to start measuring the LFCT while the test subject remains in a resting state. As one example, this instruction to start measurement is performed by the test subject or a measurement technician issuing an instruction to start measurement through the touch panel of the display 22 or the like.

In step 106, the correction unit 31 instructs the test subject to start holding one's breath. Specifically, for example, the correction unit 31 may cause the display 22 to display a message such as "Please hold your breath.", or output an instruction as speech.

In step 108, after a fixed period elapses (for example, after 20 seconds elapse) since the start of the breath holding, the correction unit 31 instructs the test subject to resume breathing. Specifically, for example, the correction unit 31 causes the display 22 to display a message indicating the resumption of breathing by a countdown, or output an instruction as speech. Additionally, an indication that one has resumed breathing may also be input by an operation (such as an operation of pressing a button) by the test subject oneself.

In step 110, the correction unit 31 determines whether or not a predetermined time has elapsed since the resumption of breathing. The predetermined time is preset as a duration for observation over time, and may be 60 seconds or the like, for example. Note that since the arrival time of oxygen is different depending on the measurement site, a duration for observation over time that is suited to the measurement site is preferably preset. In the case of determining that the predetermined time has elapsed (the case of a positive determination), the flow proceeds to step 112, whereas in the case of determining that the predetermined time has not yet elapsed (the case of a negative determination), the flow stands by in step 110.

In step 112, the correction unit 31 performs a correction by multiplying IR(t) or Red(t) obtained through the above measurement by the coefficient α derived in step 102 above. Note that in the present exemplary embodiment, the correction is performed by multiplying IR(t) by the coefficient α (ΔRed/ΔIR), but in the case of correcting Red(t), it is sufficient to set the coefficient α to ΔIR/ΔRed.

Figure 20:
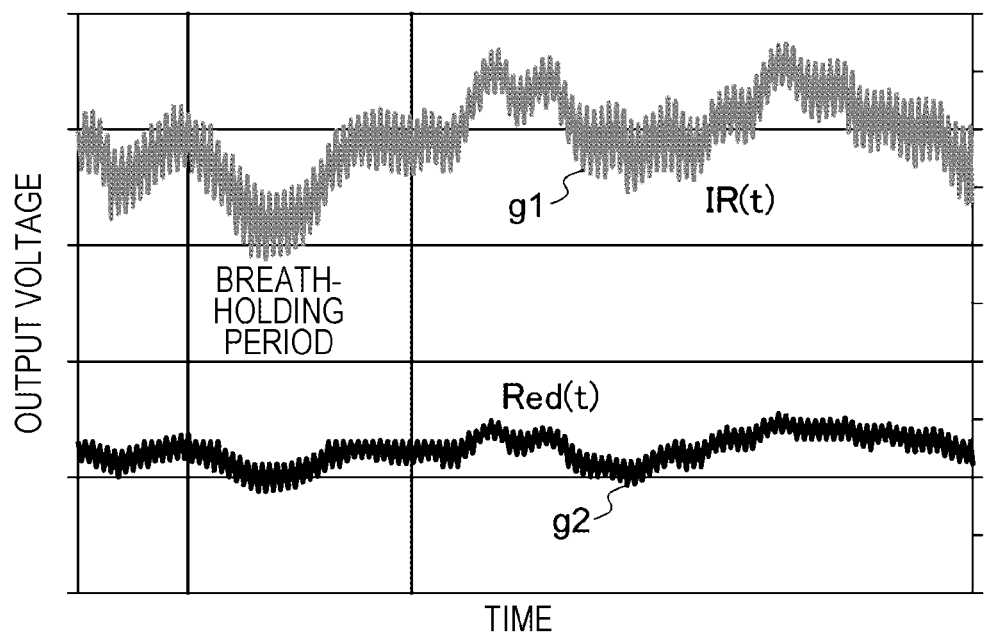
FIG. 20 is a graph illustrating one example of time series data of an IR light signal and time series data of a red light signal according to the present exemplary embodiment.

FIG. 20 is a graph illustrating one example of time series data of the IR light signal and time series data of the red light signal according to the present exemplary embodiment.

Note that in FIG. 20, the vertical axis represents the output voltage of the light receiver 3 while the horizontal axis represents time.

As illustrated in FIG. 20, the graph g1 represents IR(t), which is the time series data of the IR light signal. Also, the graph g2 represents Red(t), which is the time series data of the red light signal.

Figure 21:
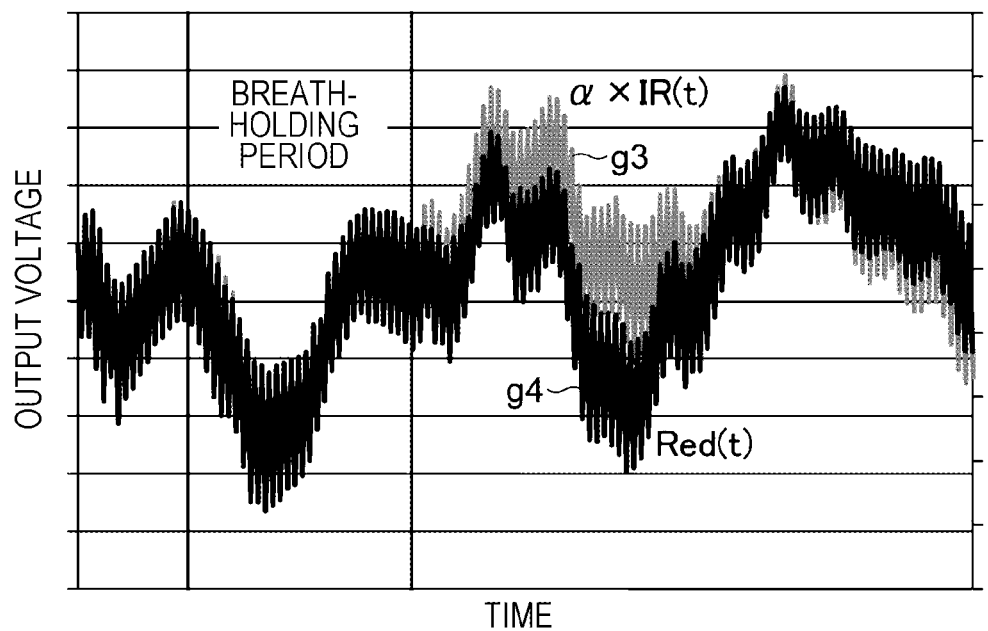
FIG. 21 is a graph illustrating one example of time series data of an IR light signal and time series data of a red light signal after correction according to the present exemplary embodiment.

FIG. 21 is a graph illustrating one example of the time series data of the IR light signal and the time series data of the red light signal after correction according to the present exemplary embodiment.

Note that in FIG. 21, the vertical axis represents the output voltage of the light receiver 3 while the horizontal axis represents time.

As illustrated in FIG. 21, the graph g3 represents the offset-adjusted α×IR(t) obtained by multiplying IR(t) by the coefficient α. Also, the graph g4 represents Red(t), which is the time series data of the red light signal.

Note that the instruction to resume breathing in step 108 above may also be issued in the case of detecting a drop in the blood oxygen concentration.

Figure 22:
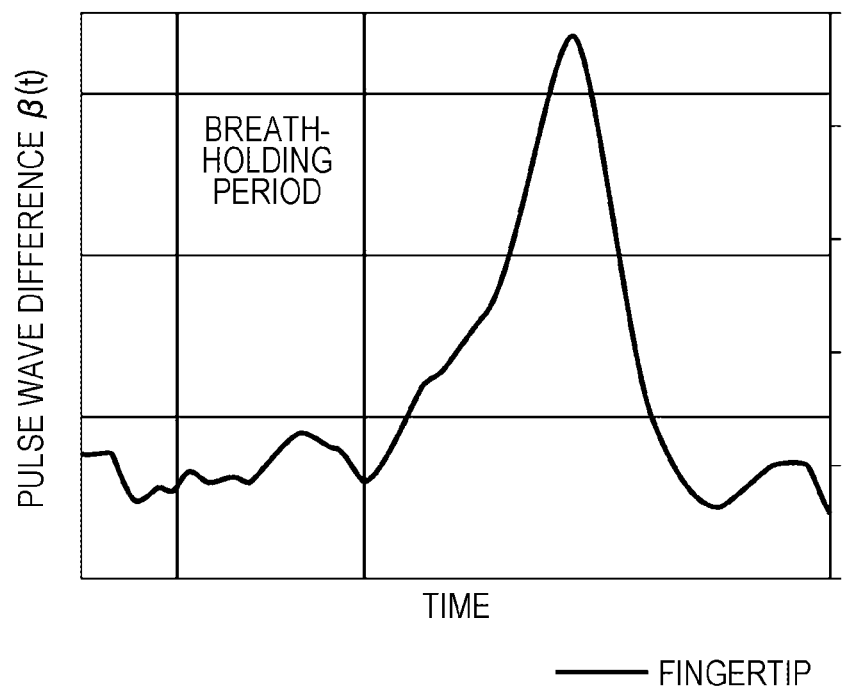
FIG. 22 is a graph illustrating one example of a monitor result by the pulse wave difference according to the present exemplary embodiment.

FIG. 22 is a graph illustrating one example of a monitor result by the pulse wave difference according to the present exemplary embodiment.

Figure 23:
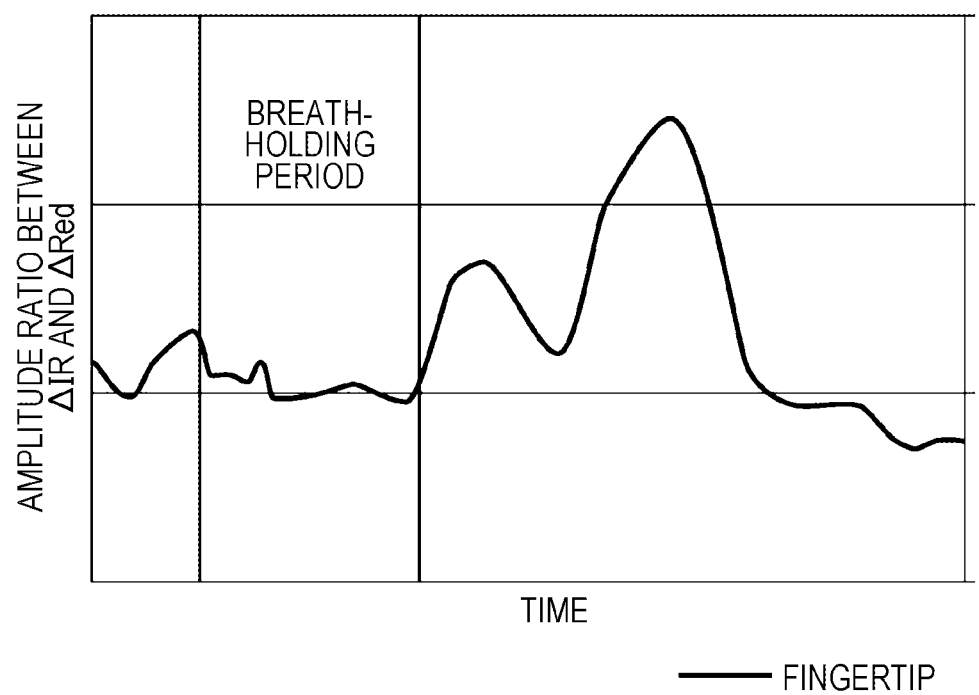
FIG. 23 is a graph illustrating one example of a monitor result obtained by detecting a change in the amplitude ratio of a pulse wave as a change in the blood oxygen concentration according to the related art.

In FIG. 22, the vertical axis represents the pulse wave difference β(t) while the horizontal axis represents time. Also, FIG. 23 is a graph illustrating one example of a monitor result obtained by detecting a change in the amplitude ratio of the pulse wave as a change in the blood oxygen concentration according to the related art. In FIG. 23, the vertical axis represents the amplitude ratio of ΔIR and ΔRed while the horizontal axis represents time.

As demonstrated by FIGS. 22 and 23, with the method according to the present exemplary embodiment (FIG. 22), compared to the method of the related art (FIG. 23), the change in oxygen saturation due to holding breath is exhibited distinctly.

Next, in step 114, the computing unit 32 uses Formula (7) above to compute the pulse wave difference β(t) from α×IR(t) obtained by the correction in step 112 and Red(t).

Note that in the case of correcting Red(t), it is sufficient to use Formula (8) above to compute the pulse wave difference β(t).

In step 116, the detection unit 33 detects the inflection point of the blood oxygen concentration associated with a change in the amount of oxygen inhaled by the test subject on the basis of the pulse wave difference β(t) computed in step 114.

In step 118, the specification unit 34 specifies the amount of time from the point in time at which the amount of oxygen inhaled by the test subject changed until the inflection point detected in step 116 as the LFCT, and ends the series of processes according to the biological information measurement program. Note that in the present exemplary embodiment, the process goes up to the specification of the LFCT, but in addition, Formula (6) above may be applied to the specified LFCT to compute the cardiac output, which is one example of output.

Figure 24:
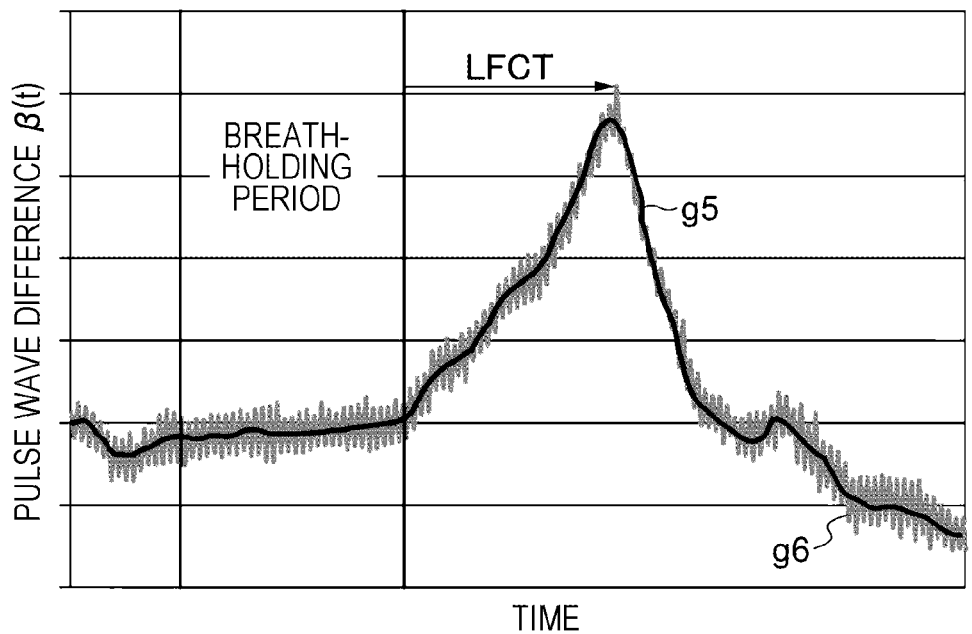
FIG. 24 is a graph illustrating one example of the LFCT specified from the pulse wave difference according to the present exemplary embodiment.
Figure 25:
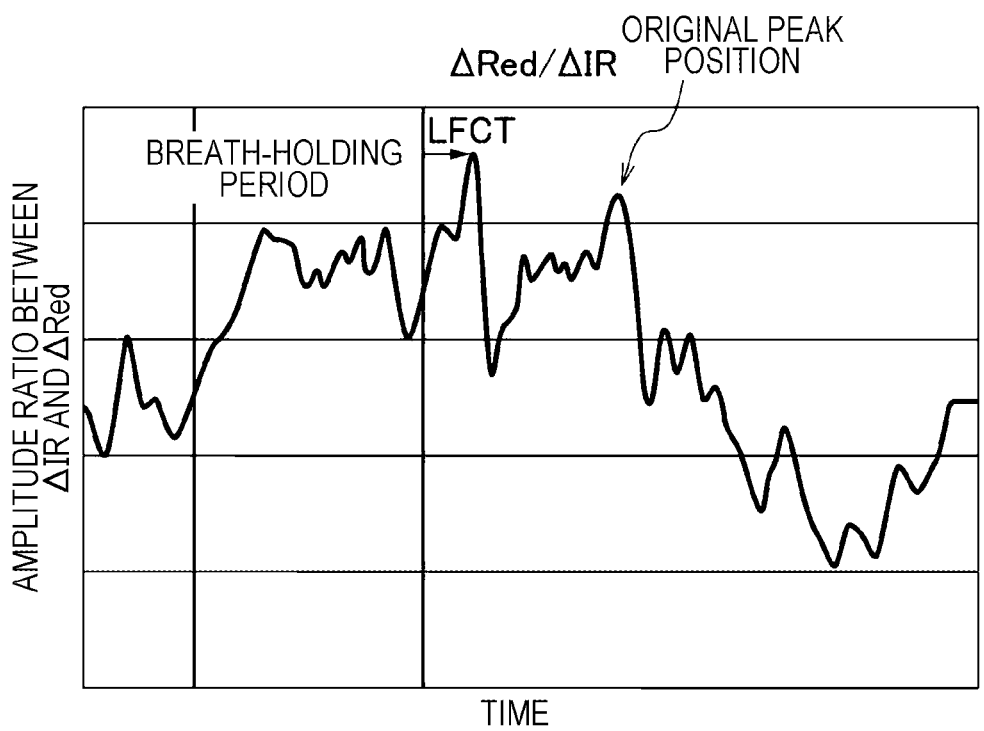
FIG. 25 is a graph illustrating the LFCT specified from the amplitude ratio according to a comparative example.

FIG. 24 is a graph illustrating one example of the LFCT specified from the pulse wave difference β(t) according to the present exemplary embodiment. In FIG. 24, the vertical axis represents the pulse wave difference β(t) while the horizontal axis represents time. Also, FIG. 25 is a graph illustrating the LFCT specified from the amplitude ratio according to a comparative example. In FIG. 25, the vertical axis represents the amplitude ratio of ΔIR and ΔRed while the horizontal axis represents time.

As illustrated in FIG. 24, the LFCT is taken to be the amount of time from the point in time at which breathing resumes until the inflection point indicated by the maximum value of the pulse wave difference β(t) (=α×IR(t)−Red(t)).

Note that in FIG. 24, the graph g5 represents the pulse wave difference β(t) as a moving average of sample n data (in this example, n=64). Also, the graph g6 represents the pulse wave difference β(t) in the case of setting the coefficient α=0.3583. In this way, by treating the pulse wave difference β(t) as a moving average of sample n data, residual pulse wave components due to differences in blood oxygen concentration are removed, and a more accurate LFCT is obtained.

Also, the graph g5 and the graph g6 illustrated in FIG. 24 demonstrate that immediately after the breath-holding period ends and breathing is resumed, the value of the pulse wave difference β(t) rises, reaches a single peak, and then falls. Since the pulse wave difference β(t) rises as the blood oxygen concentration falls, the point in time of the peak is the state of the lowest blood oxygen concentration, and the inflection point where the pulse wave difference β(t) beings to fall indicates that oxygen is starting to be taken into the blood due to the resumption of breathing. Consequently, the amount of time from the resumption of breathing up to the peak is specified as the LFCT.

On the other hand, in the comparative example illustrated in FIG. 25, the LFCT is specified from the amplitude ratio (ΔRed/ΔIR). For this reason, for example, in the case of a test subject with a small amplitude ratio or the like, a peak position different from the original peak position may be detected, and the LFCT may not be specified accurately in some cases.

In this way, according to the present exemplary embodiment, compared to the case of using the amplitude ratio of two pulse wave signals of different wavelengths, change in the blood oxygen concentration are measured accurately.

Second Exemplary Embodiment

The first exemplary embodiment above describes an embodiment that uses the pulse wave difference β(t) representing change in the blood oxygen concentration to accurately measure change in the blood oxygen concentration. In the present exemplary embodiment, by additionally removing the pulse wave component from each pulse wave signal before correction, the accuracy of measuring change in the blood oxygen concentration is improved further.

Figure 26:
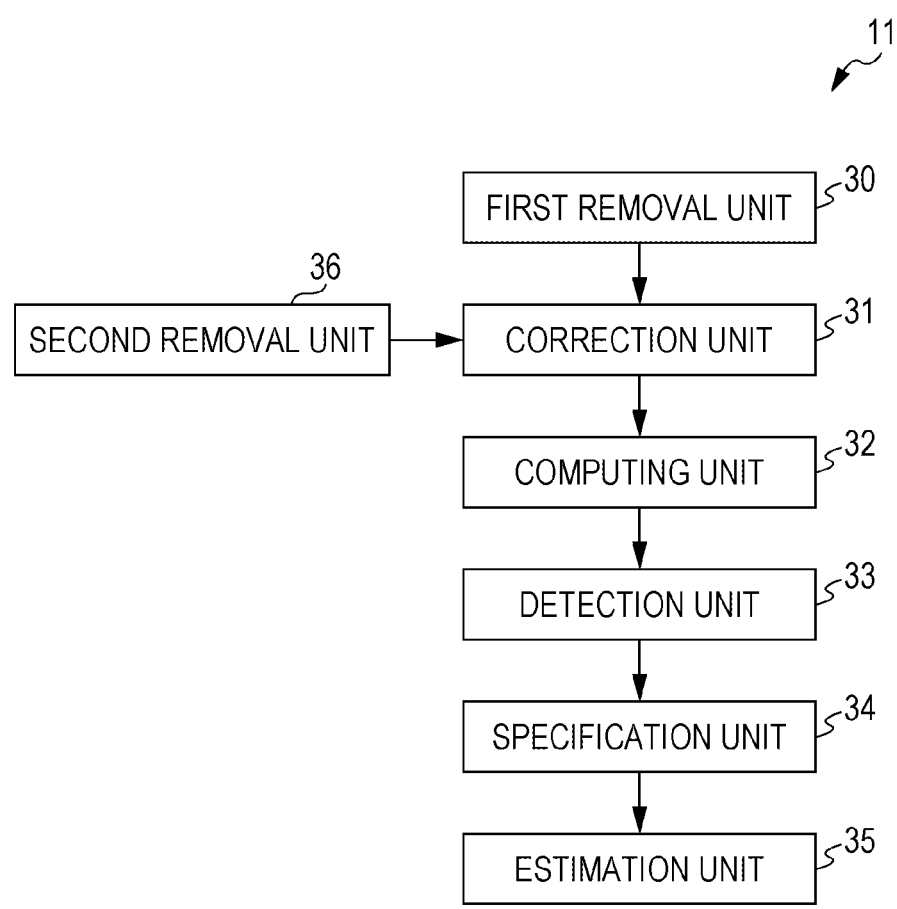
FIG. 26 is a block diagram illustrating one example of a functional configuration of the biological information measurement device according to a second exemplary embodiment.

FIG. 26 is a block diagram illustrating one example of a functional configuration of a biological information measurement device 11 according to a second exemplary embodiment.

As illustrated in FIG. 26, the biological information measurement device 11 according to the present exemplary embodiment is provided with the first removal unit 30, the correction unit 31, the computing unit 32, the detection unit 33, the specification unit 34, and the estimation unit 35 described above, as well as a second removal unit 36. Note that structural elements having the same function as the biological information measurement device 10 according to the first exemplary embodiment are denoted with the same signs, and a repeated description is omitted here.

The second removal unit 36 according to the present exemplary embodiment removes at least a part of a frequency component corresponding to change in the amount of arterial blood in the living body 8 from each of the IR light signal and the red light signal output from the light receiver 3, and outputs each of the IR light signal and the red light signal with the at least part of the frequency component removed to the correction unit 31. As one example, a low-pass filter (LPF) is applied as the second removal unit.

The correction unit 31 according to the present exemplary embodiment receives the IR light signal and the red light signal from which at least part of the frequency component has been removed by the second removal unit 36.

Figure 27:
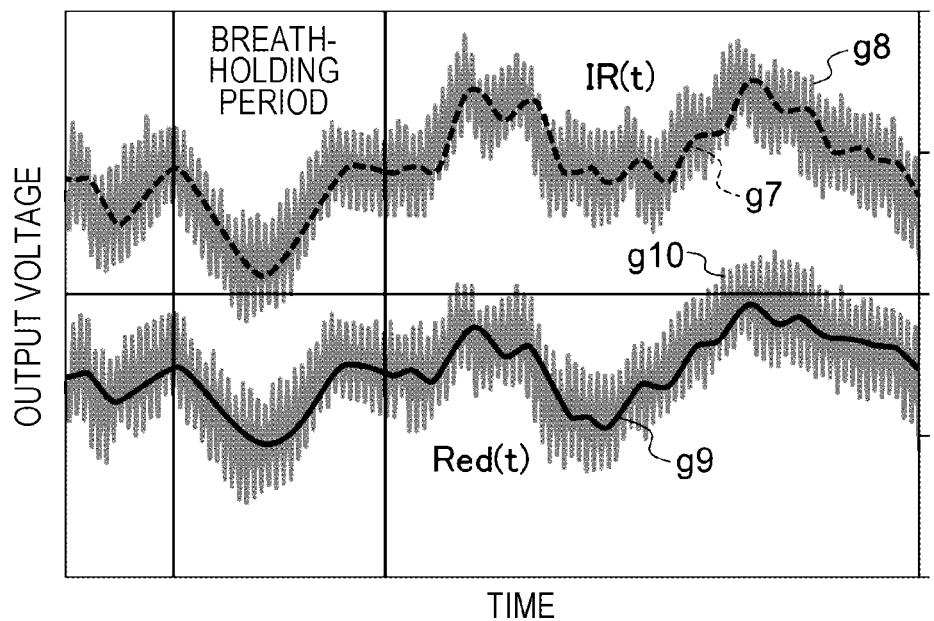
FIG. 27 is a graph illustrating one example of time series data of an IR light signal and time series data of a red light signal to which an LPF is applied according to the present exemplary embodiment.

FIG. 27 is a graph illustrating one example of time series data of the IR light signal and time series data of the red light signal to which an LPF is applied according to the present exemplary embodiment.

Note that in FIG. 27, the vertical axis represents the output voltage of the light receiver 3 while the horizontal axis represents time.

As illustrated in FIG. 27, the graph g7 represents IR(t) that is the time series data of the IR light signal after applying the LPF. Also, the graph g8 represents IR(t) that is the time series data of the IR light signal before applying the LPF. The graph g9 represents Red(t) that is the time series data of the red light signal after applying the LPF. Also, the graph g10 represents Red(t) that is the time series data of the red light signal before applying the LPF. Note that herein, a second-order Bessel filter is used as one example of the LPF. Also, with respect to the pulse frequency (herein, 1.6 Hz), the cutoff frequency of the LPF is set to ⅛ (herein, 0.2 Hz).

Figure 28:
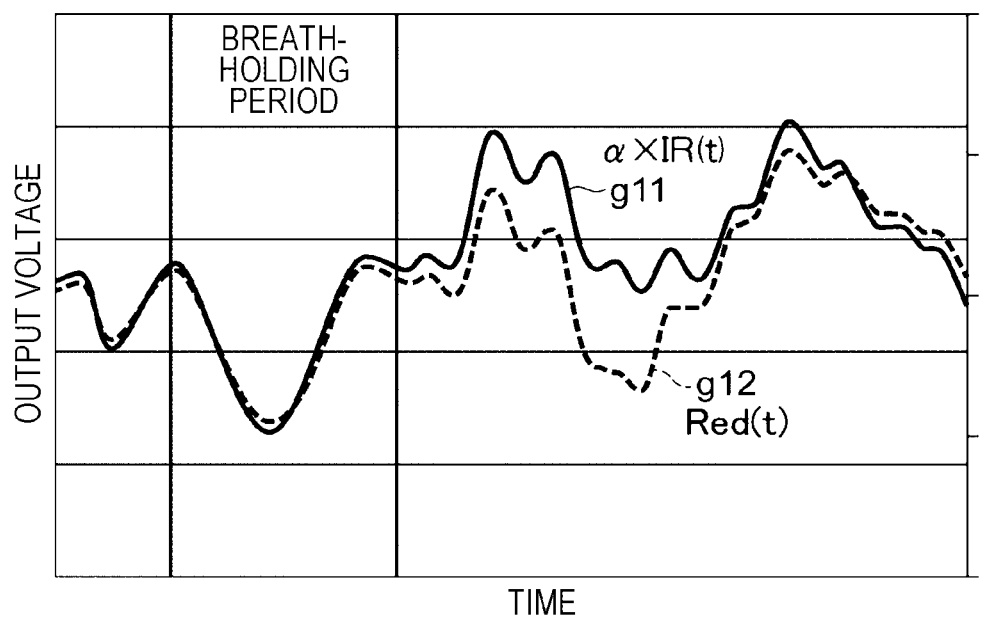
FIG. 28 is a graph illustrating one example of time series data of an IR light signal and time series data of a red light signal after correction according to the present exemplary embodiment.

FIG. 28 is a graph illustrating one example of the time series data of the IR light signal and the time series data of the red light signal after correction according to the present exemplary embodiment.

Note that in FIG. 28, the vertical axis represents the output voltage of the light receiver 3 while the horizontal axis represents time.

As illustrated in FIG. 28, the graph g11 represents the offset-adjusted α×IR(t) obtained by multiplying IR(t) with the LPF applied by the coefficient α. Also, the graph g12 represents Red(t), which is the time series data of the red light signal.

Figures 29A, 29B, 29C, 29D:
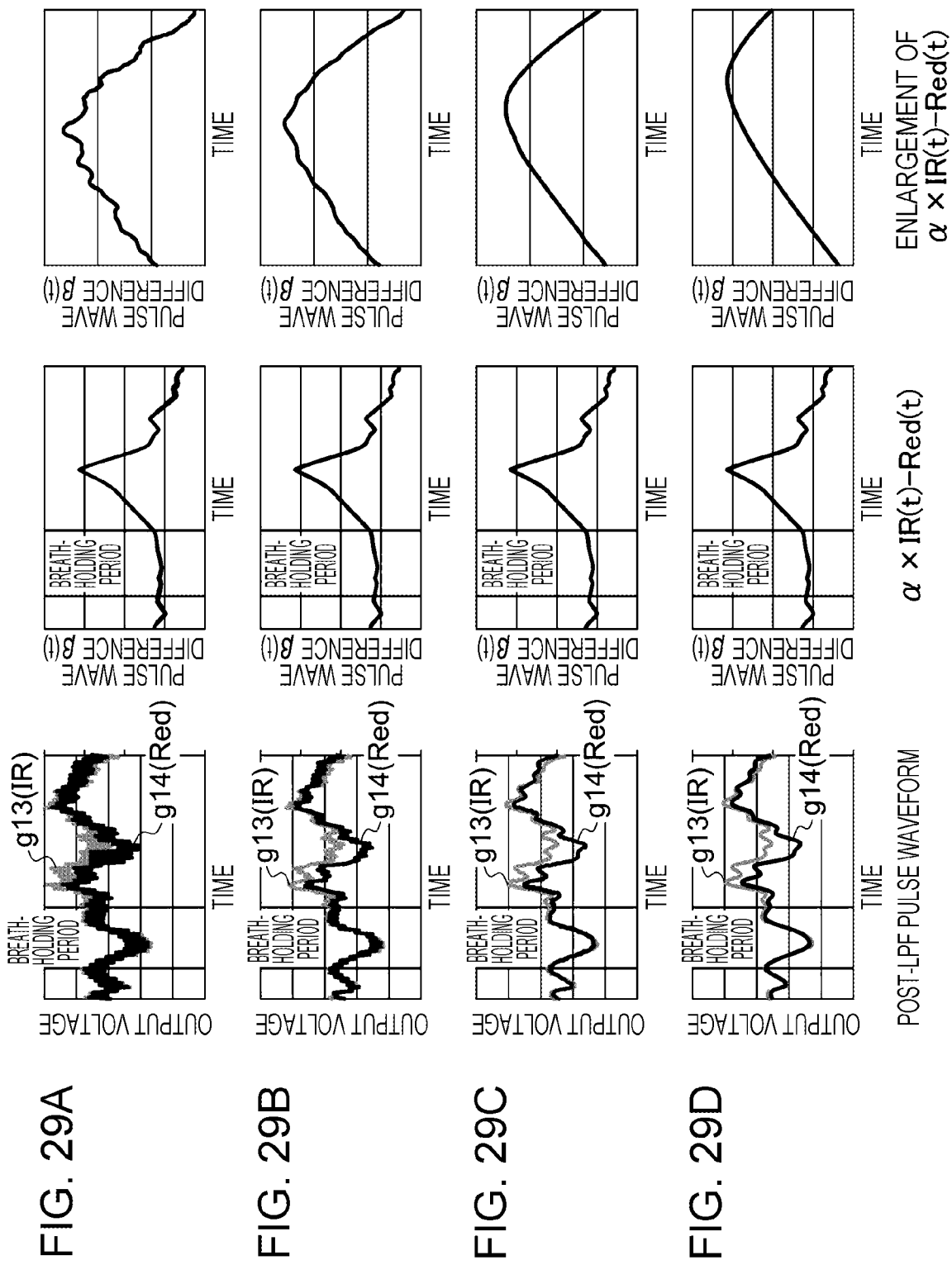
FIG. 29A is a graph illustrating the post-LPF pulse waveform, the pulse wave difference, and an enlargement of the pulse wave difference in the case of making the cutoff frequency of the LPF equal to the pulse frequency according to the present exemplary embodiment.
FIG. 29B is a graph illustrating the post-LPF pulse waveform, the pulse wave difference, and an enlargement of the pulse wave difference in the case of making the cutoff frequency of the LPF equal to ½ the pulse frequency according to the present exemplary embodiment.
FIG. 29C is a graph illustrating the post-LPF pulse waveform, the pulse wave difference, and an enlargement of the pulse wave difference in the case of making the cutoff frequency of the LPF equal to ¼ the pulse frequency according to the present exemplary embodiment.
FIG. 29D is a graph illustrating the post-LPF pulse waveform, the pulse wave difference, and an enlargement of the pulse wave difference in the case of making the cutoff frequency of the LPF equal to ⅛ the pulse frequency according to the present exemplary embodiment.

FIG. 29A is a graph illustrating the post-LPF pulse waveform, the pulse wave difference β(t), and an enlargement of the pulse wave difference β(t) in the case of making the cutoff frequency of the LPF equal to the pulse frequency according to the present exemplary embodiment.

FIG. 29B is a graph illustrating the post-LPF pulse waveform, the pulse wave difference β(t), and an enlargement of the pulse wave difference β(t) in the case of making the cutoff frequency of the LPF equal to ½ the pulse frequency according to the present exemplary embodiment.

FIG. 29C is a graph illustrating the post-LPF pulse waveform, the pulse wave difference β(t), and an enlargement of the pulse wave difference β(t) in the case of making the cutoff frequency of the LPF equal to ¼ the pulse frequency according to the present exemplary embodiment.

FIG. 29D is a graph illustrating the post-LPF pulse waveform, the pulse wave difference β(t), and an enlargement of the pulse wave difference β(t) in the case of making the cutoff frequency of the LPF equal to ⅛ the pulse frequency according to the present exemplary embodiment.

Note that in FIGS. 29A to 29D, the pulse frequency is 1.6 Hz. The pulse wave difference β(t) is α×IR(t)−Red(t). The graph g13 represents the offset-adjusted α×IR(t) obtained by multiplying IR(t) with the LPF applied by the coefficient α. Also, the graph g14 represents Red(t), which is the time series data of the red light signal.

From the examples of the graphs illustrated in FIGS. 29A to 29D, it is desirable to set the cutoff frequency of the LPF to ¼ the pulse frequency or less. By setting the cutoff frequency to ¼ or less, the influence of the pulse wave is largely reduced, and the inflection point of the blood oxygen concentration is detected more accurately. Note that since the cutoff frequency produces a delay, to correct the delay time, it is desirable to have a lookup table corresponding to the cutoff frequency.

Also, instead of the LPF above, a method of using the midpoints of the pulse wave may be applied. In this case, by generating a first waveform signal that connects intermediate points corresponding to the intermediate value between the maximum value and the minimum value obtained in each cycle of the IR light signal, the second removal unit 36 removes at least a part of the frequency component corresponding to change in the amount of arterial blood in the living body 8. Similarly, by generating a second waveform signal that connects the intermediate points corresponding to the intermediate value between the maximum value and the minimum value obtained in each cycle of the red light signal, the second removal unit 36 removes at least a part of the frequency component corresponding to change in the amount of arterial blood in the living body 8.

First, the second removal unit 36 applies a smoothing filter to each of the obtained IR(t) and Red(t). In the case of applying an LPF as the smoothing filter, the approximate range of the cutoff frequency is set from 2× (herein, 3.2 Hz) to 16× (herein, 25.6 Hz) with respect to the pulse frequency (herein, 1.6 Hz). This is because if the cutoff frequency is too low, a drop in the amplitude values may occur, and if the cutoff frequency is too high, noise may not be removed in some cases.

Figure 30:
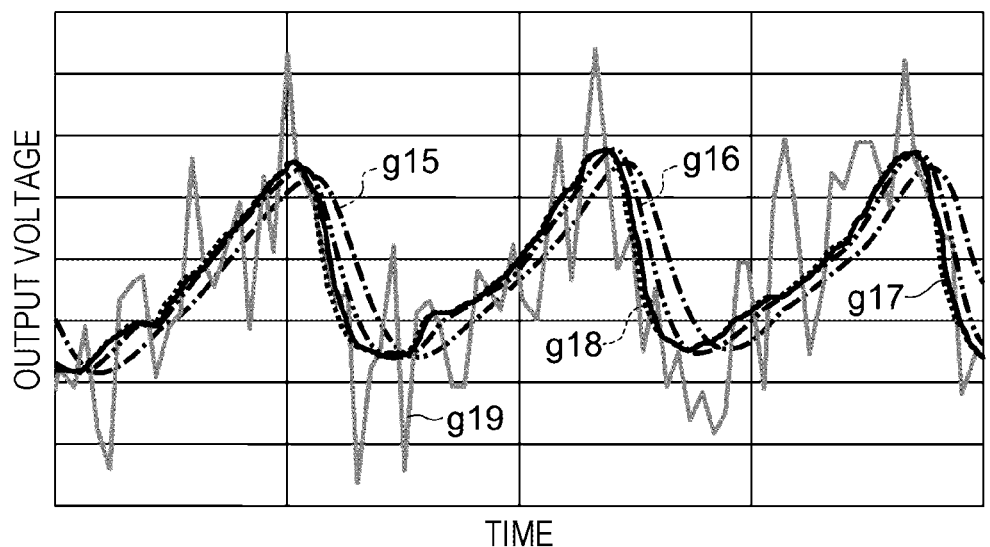
FIG. 30 is a graph illustrating one example of time series data of a red light signal to which an LPF is applied according to the present exemplary embodiment.

FIG. 30 is a graph illustrating one example of time series data of the red light signal to which an LPF is applied according to the present exemplary embodiment.

Note that in FIG. 30, the vertical axis represents the output voltage of the light receiver 3 while the horizontal axis represents time.

As illustrated in FIG. 30, the graph g15 represents Red(t) that is the time series data of the red light signal to which is applied an LPF having a cutoff frequency that is 2× the pulse frequency. Also, the graph g16 represents Red(t) that is the time series data of the red light signal to which is applied an LPF having a cutoff frequency that is 4× the pulse frequency. Also, the graph g17 represents Red(t) that is the time series data of the red light signal to which is applied an LPF having a cutoff frequency that is 8× the pulse frequency. Also, the graph g18 represents Red(t) that is the time series data of the red light signal to which is applied an LPF having a cutoff frequency that is 16× the pulse frequency. Also, the graph g19 represents Red(t) that is the time series data of the red light signal without the LPF applied.

Figure 31:
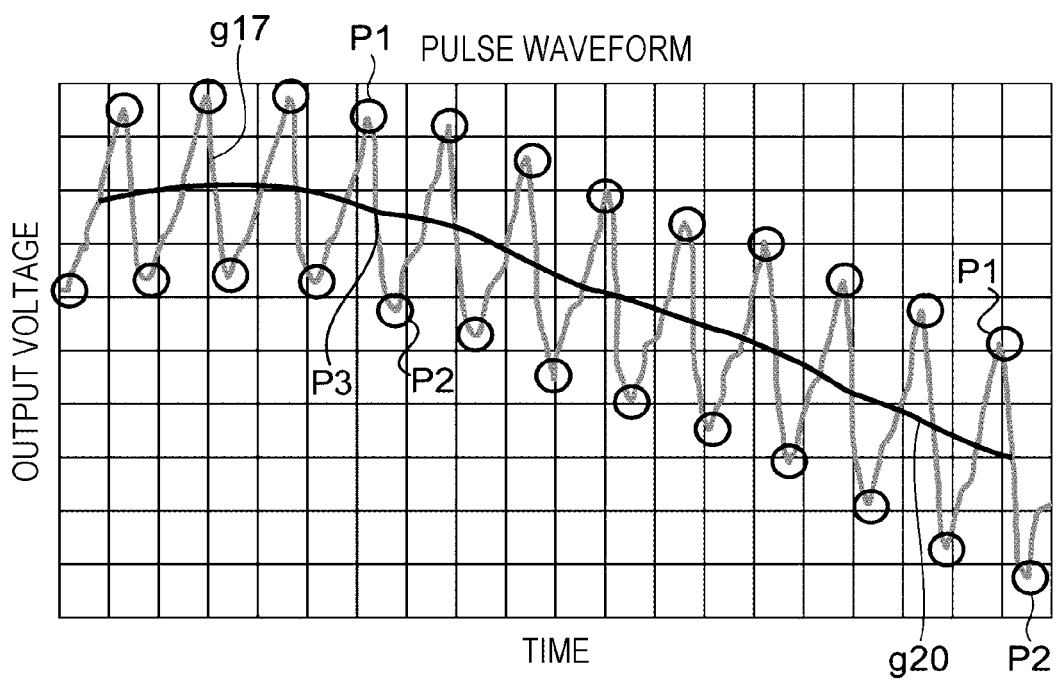
FIG. 31 is a graph illustrating one example of a midpoint waveform obtained from time series data of a red light signal after smoothing according to the present exemplary embodiment.

FIG. 31 is a graph illustrating one example of a midpoint waveform obtained from time series data of the red light signal after smoothing according to the present exemplary embodiment.

Note that in FIG. 31, the vertical axis represents the output voltage of the light receiver 3 while the horizontal axis represents time.

Herein, the case of using the graph g17 illustrated in FIG. 30 is described as an example, but the other graphs g15, g16, and g18 may also be used.

As illustrated in FIG. 31, the second removal unit 36 detects a peak value P1 taking the maximum value and a peak value P2 taking the minimum value in each cycle of the graph g17. Note that the peak value P1 is expressed as $(t_i, y_i)$, and the peak value P2 is expressed as $(t_{i+1}, y_{i+1})$. If (t, y) is taken to be the intermediate value P3 between adjacent peak values P1 and P2, the intermediate value P3 may be computed according to Formula (9) indicated below.

(Math. 9)

$$t=(t_i+t_{i+1})/2, y=(y_i+y_{i+1})/2 \qquad (9)$$

Additionally, by connecting the intermediate points corresponding to the intermediate values P3 computed according to Formula (9) above, the second removal unit 36 generates the midpoint waveform g20, which is one example of the second waveform signal. In this way, a second waveform signal is generated for Red(t), but a first waveform signal for IR(t) is also generated by a similar technique.

Figure 32:
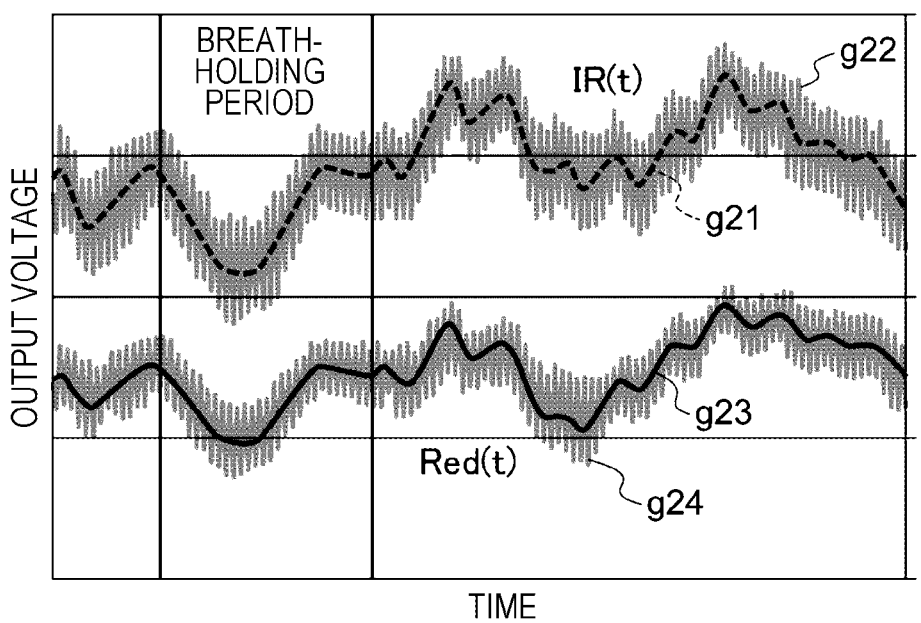
FIG. 32 is a graph illustrating one example of time series data of an IR light signal and time series data of a red light signal connecting the pulse wave midpoints according to the present exemplary embodiment.

FIG. 32 is a graph illustrating one example of time series data of the IR light signal and time series data of the red light signal connecting the pulse wave midpoints according to the present exemplary embodiment.

Note that in FIG. 32, the vertical axis represents the output voltage of the light receiver 3 while the horizontal axis represents time.

As illustrated in FIG. 32, the graph g21 represents IR(t) that is the time series data of the IR light signal connecting the pulse wave midpoints. Also, the graph g22 represents IR(t) that is the time series data of the IR light signal before connecting the pulse wave midpoints. The graph g23 represents Red(t) that is the time series data of the red light signal connecting the pulse wave midpoints. Also, the graph g24 represents Red(t) that is the time series data of the red light signal before connecting the pulse wave midpoints.

Figure 33:
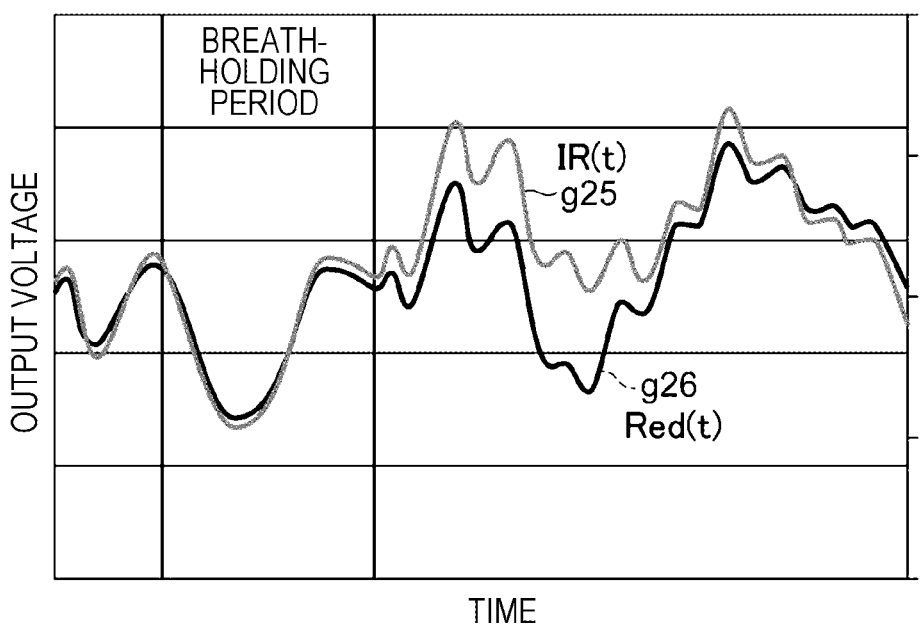
FIG. 33 is a graph illustrating one example of time series data of an IR light signal and time series data of a red light signal after correction according to the present exemplary embodiment.

FIG. 33 is a graph illustrating one example of the time series data of the IR light signal and the time series data of the red light signal after correction according to the present exemplary embodiment.

Note that in FIG. 33, the vertical axis represents the output voltage of the light receiver 3 while the horizontal axis represents time.

As illustrated in FIG. 33, the graph g25 represents the offset-adjusted α×IR(t) obtained by multiplying IR(t) connecting the pulse wave midpoints by the coefficient α. Also, the graph g26 represents Red(t), which is the time series data of the red light signal.

Figure 34:
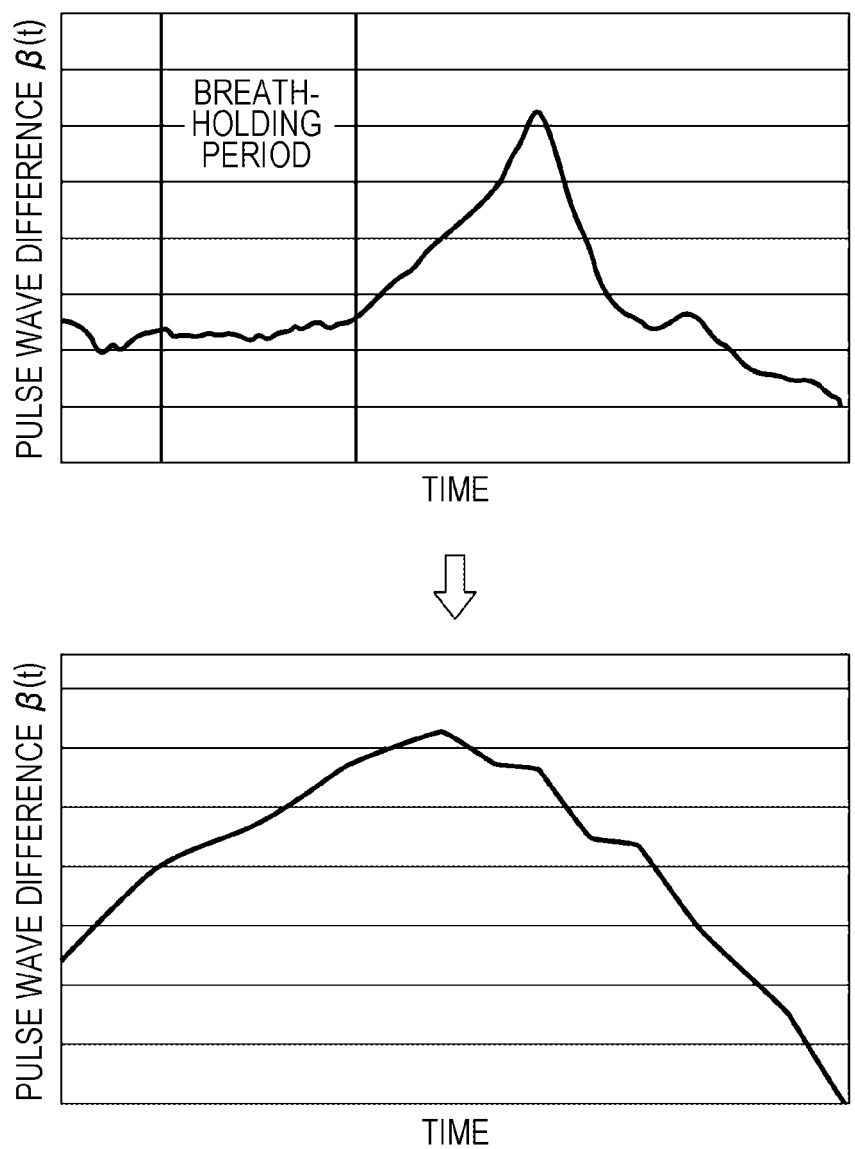
FIG. 34 is a graph illustrating the pulse wave difference and an enlargement of the pulse wave difference obtained from a pulse waveform connecting the pulse wave midpoints according to the present exemplary embodiment.

FIG. 34 is a graph illustrating the pulse wave difference β(t) and an enlargement of the pulse wave difference β(t) obtained from a pulse waveform connecting the pulse wave midpoints according to the present exemplary embodiment.

Note that in FIG. 34, the vertical axis represents the pulse wave difference β(t) while the horizontal axis represents time.

In the example illustrated in FIG. 34, the pulse wave difference β(t) is α×IR(t)−Red(t).

In this way, according to the present exemplary embodiment, by using the LPF or the pulse wave midpoints to remove the pulse wave component from each pulse wave signal before correction, change in the blood oxygen concentration is measured even more accurately.

The above describes a biological information measurement device as one example of an exemplary embodiment. An exemplary embodiment may also be configured as a program that causes a computer to execute the functions of each component provided in the biological information measurement device. An exemplary embodiment may also be configured as a computer-readable storage medium storing the program.

Otherwise, the configuration of the biological information measurement device described in the exemplary embodiment above is an example, and may be modified according to circumstances within a range that does not depart from the gist.

Also, the process flow of the program described in the exemplary embodiment above is an example, and unnecessary steps may be removed, new steps may be added, or the processing sequence may be rearranged within a range that does not depart from the gist.

Also, the exemplary embodiment above describes a case in which the process according to the exemplary embodiment is realized by a software configuration using a computer by executing a program, but the configuration is not limited thereto. An exemplary embodiment may also be realized by a hardware configuration, or by a combination of a hardware configuration and a software configuration, for example.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A biological information measurement device comprising:
   a memory;
   a display; and
   a processor communicatively coupled to the memory and the display, wherein the processor is configured to:
      receive a first signal expressing a change in an amount of light of a first wavelength detected from a living body and a second signal expressing a change in an amount of light of a second wavelength detected from the living body,
      correct at least one of the first signal and the second signal to reduce a difference between an amount of change in the first signal and an amount of change in the second signal associated with a change in an amount of arterial blood of the living body by calculating a pulse wave difference, and
      compute a change in a blood oxygen concentration in the living body on a basis of the first signal and the second signal of which at least one is corrected,
   wherein a corrected signal is obtained by multiplying a value of a plurality of the first signal or a value of a plurality of the second signal by a coefficient expressed as an amplitude ratio of the amount of change in the first signal and the amount of change in the second signal, and
   wherein the pulse wave difference is calculated by subtracting the plurality of the second signals from the corrected signal.

2. The biological information measurement device according to claim 1, wherein
   the correction is a correction that makes the amount of change in the first signal and the amount of change in the second signal equal.

3. The biological information measurement device according to claim 1, wherein
   the change in the blood oxygen concentration is expressed by a difference between a value of the first signal and a value of the second signal of which at least one is corrected by the processor.

4. The biological information measurement device according to claim 3, wherein:
   the processor detects an inflection point in the blood oxygen concentration associated with a change in an amount of oxygen inhaled by the living body, on a basis of the difference expressing the change in the blood oxygen concentration.

5. The biological information measurement device according to claim 4, wherein:
   the processor specifies an amount of time from a point in time at which the amount of oxygen inhaled by the living body changes until the inflection point in the blood oxygen concentration detected.

6. The biological information measurement device according to claim 1, wherein
   the coefficient is expressed as an amplitude ratio of the amplitude of the first signal and the amplitude of the second signal before causing the amount of oxygen inhaled by the living body to change, and
   the correction is performed by multiplying the coefficient by a value of the first signal or a value of the second signal after causing the amount of oxygen inhaled by the living body.

7. The biological information measurement device according to claim 1, wherein:
   a first filter removes a direct-current component from each of a first received light signal corresponding to light of the first wavelength and a second received light signal corresponding to light of the second wavelength output from a light receiver, and outputs each of the first received light signal and the second received light signal with the direct-current component removed as each of the first signal and the second signal, and
   derive a coefficient expressed as an amplitude ratio of an amplitude of the first signal and an amplitude of the second signal on a basis of the first signal and the second signal received.

8. The biological information measurement device according to claim 7, wherein the correction is performed by multiplying the derived coefficient by a value of a first signal or a value of a second signal received from the light receiver without going through the first filter.

9. The biological information measurement device according to claim 7, wherein
the correction is performed by multiplying the derived coefficient by a value of a first signal or a value of a second signal received from the light receiver without going through the first filter.

10. The biological information measurement device according to claim 1, further comprising:
a second filter that removes at least a part of a frequency component corresponding to the change in an amount of arterial blood in the living body from each of a first received light signal corresponding to light of the first wavelength and a second received light signal corresponding to light of the second wavelength output from a light receiver, and outputs each of the first received light signal and the second received light signal with the at least a part of the frequency component removed as each of the first signal and the second signal.

11. The biological information measurement device according to claim 10, wherein
the second filter is a low-pass filter.

12. The biological information measurement device according to claim 10, wherein
the second filter
removes at least a part of the frequency component corresponding to the change in the amount of arterial blood in the living body by generating a first waveform signal that connects intermediate points corresponding to an intermediate value between a maximum value and a minimum value obtained in each cycle of the first received light signal, and
removes at least a part of the frequency component corresponding to a change in the amount of arterial blood in the living body by generating a second waveform signal that connects intermediate points corresponding to an intermediate value between a maximum value and a minimum value obtained in each cycle of the second received light signal.

13. A biological information measurement device comprising:
a memory;
a display; and
a processor communicatively coupled to the memory and the display, wherein the processor is configured to:
receive a first signal expressing a change in an amount of light of a first wavelength detected from a living body and a second signal expressing a change in an amount of light of a second wavelength detected from the living body, and
correct at least one of the first signal and the second signal to reduce a difference between an amount of change in the first signal and an amount of change in the second signal associated with a change in an amount of arterial blood of the living body by calculating a pulse wave difference, and
detects, after an amount of oxygen inhaled by the living body changes, an inflection point in a blood oxygen concentration obtained from the first signal and the second signal of which at least one is corrected,
wherein a corrected signal is obtained by multiplying a value of a plurality of the first signal or a value of a plurality of the second signal by a coefficient expressed as an amplitude ratio of the amount of change in the first signal and the amount of change in the second signal, and
wherein the pulse wave difference is calculated by subtracting the plurality of the second signals from the corrected signal.

14. A non-transitory computer readable medium storing a program causing a computer to execute a process for measuring biological information, the process comprising:
receiving a first signal expressing a change in an amount of light of a first wavelength detected from a living body and a second signal expressing a change in an amount of light of a second wavelength detected from the living body;
correcting at least one of the first signal and the second signa to reduce a difference between an amount of change in the first signal and an amount of change in the second signal associated with a change in an amount of arterial blood of the living body by calculating a pulse wave difference; and
computing a change in a blood oxygen concentration in the living body on a basis of the first signal and the second signal of which at least one is corrected,
wherein a corrected signal is obtained by multiplying a value of a plurality of the first signal or a value of a plurality of the second signal by a coefficient expressed as an amplitude ratio of the amount of change in the first signal and the amount of change in the second signal, and
wherein the pulse wave difference is calculated by subtracting the plurality of the second signals from the corrected signal.

* * * * *